US008936753B2

(12) United States Patent  (10) Patent No.: US 8,936,753 B2
Yamamoto et al.  (45) Date of Patent: Jan. 20, 2015

(54) BLOOD COAGULATION ANALYZER, BLOOD COAGULATION ANALYSIS METHOD, AND COMPUTER PROGRAM PRODUCT

(75) Inventors: Norimasa Yamamoto, Kobe (JP); Hiroyuki Fujino, Kakogawa (JP); Takamichi Naito, Kobe (JP); Naohiko Matsuo, Kobe (JP); Susumu Hoshiko, Kobe (JP)

(73) Assignee: Sysmex Corporation (JP)

( * ) Notice: Subject to any disclaimer, the term of this patent is extended or adjusted under 35 U.S.C. 154(b) by 0 days.

(21) Appl. No.: 12/893,640

(22) Filed: Sep. 29, 2010

(65) Prior Publication Data

US 2011/0014640 A1 Jan. 20, 2011

Related U.S. Application Data

(63) Continuation of application No. PCT/JP2009/056059, filed on Mar. 26, 2009.

(30) Foreign Application Priority Data

Mar. 31, 2008 (JP) ................................ 2008-089670
Mar. 31, 2008 (JP) ................................ 2008-089712

(51) Int. Cl.
*G01N 33/00* (2006.01)
*G01N 21/59* (2006.01)
(Continued)

(52) U.S. Cl.
CPC ........ *G01N 21/5907* (2013.01); *G01N 33/4905* (2013.01); *G01N 33/86* (2013.01);
(Continued)

(58) Field of Classification Search
CPC ... G01N 33/4905; G01N 21/82; G01N 33/86; G01N 15/12; G01N 15/1459; G01N 2015/0073; G01N 2015/0076; G01N 2015/008; G01N 2015/1486; G01N 2021/825; G01N 21/272; G01N 35/00594; G01N 21/5907; G01N 2333/75; G01N 2015/0084; G01N 33/5094; G01N 15/14; G01N 15/1456; G01N 2015/0065; G01N 2015/1493; G01N 2035/1032; G01N 15/0205; G01N 15/0227; G01N 15/1404; G01N 15/1434; G01N 15/1463; G01N 15/147; G01N 1/14; G01N 1/38; G01N 2015/0069; G01N 2015/025; G01N 2015/1037; G01N 2015/1413; G01N 2015/1452; G01N 2015/1477; G01N 2015/149; G01N 2021/4704; G01N 2021/4707; G01N 2021/6439; G01N 2035/00356; G01N 2035/00524; G01N 2035/00544; G01N 21/21; G01N 21/6445; G01N 33/49; G01N 33/491; G01N 33/721; G01N 33/80; G01N 35/0092; G01N 35/10; G01N 35/1004; G01N 35/109; G01N 35/00603
USPC .................. 422/73, 500–504, 507, 520–522; 436/10, 180

See application file for complete search history.

(56) References Cited

U.S. PATENT DOCUMENTS 5,350,676 A * 9/1994 Oberhardt et al. .............. 435/13
5,670,329 A 9/1997 Oberhardt
(Continued)

FOREIGN PATENT DOCUMENTS

CN 101151534 A 3/2008
JP 60-058555 A 4/1985
(Continued)

OTHER PUBLICATIONS

International Search Report for International Application No. PCT/JP2009/056059, dated May 19, 2009, 3 pages.
(Continued)

*Primary Examiner* — Dean Kwak
(74) *Attorney, Agent, or Firm* — Brinks Gilson & Lione

(57) ABSTRACT

A blood coagulation analyzer includes a detector and a controller. The detector includes a light source for emitting light to a prepared measurement sample and a light-receiving section for receiving light transmitted through the measurement sample. The controller is configured to performs operations comprising acquiring, based on the light detected by the detector, ratio information reflecting a ratio between a first value reflecting the intensity of the light transmitted through the measurement sample of a clotting reaction starting stage and a second value reflecting the intensity of the light transmitted through the measurement sample of a clotting reacting ending stage, and acquiring, based on the ratio information, a fibrinogen concentration in the blood sample.

12 Claims, 16 Drawing Sheets

(51) Int. Cl.
*G01N 33/49* (2006.01)
*G01N 33/86* (2006.01)
*G01N 35/00* (2006.01)

(52) U.S. Cl.
CPC .............................. *G01N 35/00603* (2013.01)
USPC ............ 422/73; 422/500; 422/501; 422/502; 422/503; 422/504; 422/507; 422/520; 422/521; 422/522; 436/10; 436/180

(56) References Cited

U.S. PATENT DOCUMENTS

| | | | |
|---|---|---|---|
| 2001/0006819 A1 | 7/2001 | Kawamura | |
| 2003/0138962 A1* | 7/2003 | Katayama et al. | 436/69 |
| 2008/0020481 A1* | 1/2008 | Yamamoto et al. | 436/164 |

FOREIGN PATENT DOCUMENTS

| | | |
|---|---|---|
| JP | 61-159162 A | 7/1986 |
| JP | 62-093664 A | 4/1987 |
| JP | 06-141895 A | 5/1994 |
| JP | 08-510908 A | 11/1996 |
| JP | 10-123140 A | 5/1998 |
| JP | 2001-249134 A | 9/2001 |
| WO | WO 94/28168 A1 | 12/1994 |

OTHER PUBLICATIONS

Faquan, Lin et al., "Comparison between Two Fibrinogen Measuring Methods," Chinese Journal of Primary Medicine and Pharmacy, Dec. 2003, vol. 10, No. 12, pp. 1272-1273 (with translation).

Office Action from counterpart Chinese Application No. 200980112143.9, dated Jan. 22, 2013, 23 pages (with translation).

Feng, Chen et al., "Comparison with five different method for fibrinogen assay," Journal of Clinical Laboratory Science, vol. 18, No. 1, 2000, 14 pages.

Office action from counterpart Chinese Application No. 200980112143.9, dated Aug. 21, 2013, 17 pages.

* cited by examiner

FIG. 13(a)

| Specimen number | Measurement item | | | |
|---|---|---|---|---|
| | PT | | Fbg | |
| | PT sec | dFbg | Fbg sec | Fbg |
| 10001 | 10 | 500 (mg/dL) | – | – |
| 10002 | 11.5 | 650 (mg/dL) | 7.2 | 680 (mg/dL) |
| 10003 | 12 | 120 (mg/dL) | 8.3 | 140 (mg/dL) |
| | | | | |

FIG. 13(b)

| Specimen number | Measurement item | | | |
|---|---|---|---|---|
| | PT | | Fbg | |
| | PT sec | dFbg | Fbg sec | Fbg |
| 10001 | 10 | 500 (mg/dL) | 7 | 530 (mg/dL) |
| 10002 | 11.5 | 650 (mg/dL) | 7.2 | 680 (mg/dL) |
| 10003 | 12 | 900 (mg/dL) > | ! 6 | 925 (mg/dL) |
| 10004 | 9 | 40 (mg/dL) < | ! 8 | 70 (mg/dL) |
| | | | | |

FIG. 13(c)

| Specimen number | Measurement item | | | |
|---|---|---|---|---|
| | PT | | Fbg | |
| | PT sec | dFbg | Fbg sec | Fbg |
| 10001 | 10 | 500 (mg/dL) | – | – |
| 10002 | 11.5 | 650 (mg/dL) | 7.2 | 680 (mg/dL) |
| 10003 | 12 | 900 (mg/dL) > | ! 6 | 925 (mg/dL) |
| 10004 | 9 | 40 (mg/dL) < | ! 8 | 70 (mg/dL) |
| | | | | |

BLOOD COAGULATION ANALYZER, BLOOD COAGULATION ANALYSIS METHOD, AND COMPUTER PROGRAM PRODUCT

RELATED APPLICATIONS

This application is a continuation of PCT/JP2009/056059 filed on Mar. 26, 2009, which claims priority to Japanese Application Nos. JP2008-089712 filed on Mar. 31, 2008 and JP2008-089670 filed on Mar. 31, 2008. The entire contents of these applications are incorporated herein by reference.

BACKGROUND OF THE INVENTION

1. Technical Field

The present invention relates to a blood coagulation analyzer, a blood coagulation analysis method, and a computer program product.

2. Background Art

Conventionally, there has been known a blood coagulation analyzer that optically measures a blood sample to analyze, based on the measurement result, the clotting function of the blood sample (for example, see Japanese Unexamined Patent Publication No. 58555/1985 and Japanese Unexamined Patent Publication No. 123140/1998).

According to the blood coagulation analyzers disclosed in Japanese Unexamined Patent Publication No. 58555/1985 and Japanese Unexamined Patent Publication No. 123140/1998, light is emitted to a measurement sample prepared from a blood sample and a clotting reagent (a prothrombin time (hereinafter also referred to as "PT") measurement reagent, a partial thromboplastin time (hereinafter also referred to as "PTT") measurement reagent, and an activated partial thromboplastin time (hereinafter also referred to as "APTT") measurement reagent). Then, the temporal change of the scattered light from the measurement sample is measured to thereby perform a PT measurement, a PTT measurement, or an APTT measurement.

Japanese Unexamined Patent Publication No. 58555/1985 also discloses that a blood coagulation analyzer is used to calculate a value corresponding to the fibrinogen concentration in the blood sample (hereinafter also referred to as derived fibrinogen concentration (dFbg value)), by multiplying, by a fixed coefficient, a scattered light change amount from the start of the clotting reaction to the end of the clotting reaction detected in a PT measurement or an APTT measurement for example.

It is noted that Japanese Unexamined Patent Publication No. 58555/1985 suggests that a dFbg value also can be calculated even when the temporal change of transmitted light from a measurement sample is measured and the change amount of the transmitted light from the start of the clotting reaction to the end of the clotting reaction is used.

A fibrinogen concentration is basically measured by an exclusive fibrinogen concentration measurement reagent. However, this measurement requires a lot of time and cost. To prevent this, it is very useful, as disclosed in Japanese Unexamined Patent Publication No. 58555/1985, to use the data detected in a PT measurement or an APTT measurement for example to calculate a dFbg value by computation so that the resultant value is used instead of the fibrinogen concentration.

However, when the dFbg value calculated by computation is an abnormal value deviating from a predetermined range, the dFbg value cannot be used instead of the fibrinogen concentration from the viewpoint of reliability.

On the other hand, even when the fibrinogen concentration is measured by an exclusive fibrinogen concentration measurement reagent, if the measurement result is an abnormal value such as the one deviating from a predetermined range, it is required to prepare again another measurement sample having a different dilution magnification ratio to measure again the fibrinogen concentration. This has caused a disadvantage where the time and the cost required for the measurement are increased.

Furthermore, blood samples of some subjects may include a large amount of interfering substance such as chyle and bilirubin. Thus, when a blood sample including a large amount of interfering substance is measured, the interfering substance has an influence on the change amount of scattered light and the change amount of transmitted light from the start of the clotting reaction to the end of the clotting reaction. Thus, it has been difficult to accurately calculate a dFgb value.

SUMMARY OF THE INVENTION

A first aspect of the present invention is a blood coagulation analyzer comprising:

a sample preparation section for preparing a measurement sample from a blood sample and a predetermined reagent;

a detector including a light source for emitting light to the measurement sample prepared by the sample preparation section and a light-receiving section for receiving the light from the measurement sample; and a controller configured to perform operations comprising:

controlling the sample preparation section and the detector so as to prepare a first measurement sample from a blood sample and a prothrombin time measurement reagent, a partial thromboplastin time measurement reagent, or an activated partial thromboplastin time measurement reagent and to detect light from the first measurement sample;

acquiring, based on the light detected from the first measurement sample by the detector, a derived fibrinogen concentration reflecting a fibrinogen concentration in the blood sample;

determining whether the derived fibrinogen concentration is within a predetermined range or not;

controlling the sample preparation section and the detector so as to prepare, based on the determination result, a second measurement sample from the blood sample and a fibrinogen concentration measurement reagent and to detect light from the second measurement sample; and acquiring, based on the light detected by the detector from the second measurement sample, a fibrinogen concentration in the blood sample.

A second aspect of the present invention is a blood coagulation analyzer comprising:

a sample preparation section for preparing a measurement sample from a blood sample and a predetermined reagent;

a detector including a light source for emitting light to the measurement sample prepared by the sample preparation section and a light-receiving section for receiving the light from the measurement sample; and a controller configured to perform operations comprising:

controlling the sample preparation section and the detector so as to prepare a first measurement sample from a blood sample and a prothrombin time measurement reagent, a partial thromboplastin time measurement reagent, or an activated partial thromboplastin time measurement reagent and to detect light from the first measurement sample;

acquiring, based on the light detected from the first measurement sample by the detector, a derived fibrinogen concentration reflecting a fibrinogen concentration in the blood sample;

changing, depending on the derived fibrinogen concentration, a preparation condition of a second measurement sample prepared from the blood sample and a fibrinogen concentration measurement reagent;

controlling the sample preparation section and the detector so as to prepare, based on the changed preparation condition, the second measurement sample from the blood sample and a fibrinogen concentration measurement reagent and to detect light from the second measurement sample; and acquiring, based on the light detected by the detector from the second measurement sample, a fibrinogen concentration in the blood sample.

A third aspect of the present invention is a blood coagulation analyzer comprising:

a sample preparation section for preparing a measurement sample from a blood sample and a prothrombin time measurement reagent, a partial thromboplastin time measurement reagent, or an activated partial thromboplastin time measurement reagent;

a detector including a light source for emitting light to the prepared measurement sample and a light-receiving section for receiving light transmitted through the measurement sample; and a controller configured to perform operations comprising:

acquiring, based on the light detected by the detector, ratio information reflecting a ratio between a first value reflecting the intensity of the light transmitted through the measurement sample of a clotting reaction starting stage and a second value reflecting the intensity of the light transmitted through the measurement sample of a clotting reaction ending stage; and acquiring, based on the ratio information, a fibrinogen concentration in the blood sample.

A fourth aspect of the present invention is a blood coagulation analysis method comprising steps of:

preparing a first measurement sample from a blood sample and a prothrombin time measurement reagent, a partial thromboplastin time measurement reagent, or an activated partial thromboplastin time measurement reagent;

emitting light to the first measurement sample and detecting the light from the measurement sample;

acquiring, based on the light detected from the first measurement sample, a derived fibrinogen concentration reflecting a fibrinogen concentration in the blood sample;

determining whether the derived fibrinogen concentration is within a predetermined range or not;

preparing, based on the determination result, a second measurement sample from the blood sample and a fibrinogen concentration measurement reagent;

emitting light to the second measurement sample and detecting light from the second measurement sample; and acquiring, based on the light detected from the second measurement sample, a fibrinogen concentration in the blood sample.

A fifth aspect of the present invention is a blood coagulation analysis method comprising steps of:

preparing a first measurement sample from a blood sample and a prothrombin time measurement reagent, a partial thromboplastin time measurement reagent, or an activated partial thromboplastin time measurement reagent;

emitting light to the first measurement sample and detecting the light from the measurement sample;

acquiring, based on light detected from the first measurement sample, a derived fibrinogen concentration reflecting a fibrinogen concentration in the blood sample;

changing, depending on the derived fibrinogen concentration, a preparation condition of a second measurement sample prepared from the blood sample and a fibrinogen concentration measurement reagent;

preparing, based on the changed preparation condition, the second measurement sample from the blood sample and the fibrinogen concentration measurement reagent;

emitting light to the second measurement sample and detecting light from the second measurement sample; and acquiring, based on the light detected from the second measurement sample, a fibrinogen concentration in the blood sample.

A sixth aspect of the present invention is a blood coagulation analysis method comprising steps of:

preparing a measurement sample from a blood sample and a prothrombin time measurement reagent, a partial thromboplastin time measurement reagent, or an activated partial thromboplastin time measurement reagent;

emitting light to the prepared measurement sample to detect light transmitted through the measurement sample;

acquiring, based on the detected light, ratio information reflecting a ratio between a first value reflecting the intensity of the light transmitted through the measurement sample of a clotting reaction starting stage and a second value reflecting the intensity of the light transmitted through the measurement sample of a clotting reaction ending stage; and acquiring, based on the ratio information, a fibrinogen concentration in the blood sample.

A seventh aspect of the present invention is a computer program product comprising:

a computer readable medium, and a software instructions, on the computer readable medium, for enabling a computer to perform predetermined operations, comprising:

controlling a blood coagulation analyzer so as to prepare a first measurement sample from a blood sample and a prothrombin time measurement reagent, a partial thromboplastin time measurement reagent, or an activated partial thromboplastin time measurement reagent;

controlling the blood coagulation analyzer so as to emit light to the first measurement sample to detect light from the measurement sample;

acquiring, based on the light detected from the first measurement sample, a derived fibrinogen concentration reflecting a fibrinogen concentration in the blood sample;

determining whether the derived fibrinogen concentration is within a predetermined range or not;

controlling the blood coagulation analyzer so as to prepare, based on the determination result, a second measurement sample from the blood sample and a fibrinogen concentration measurement reagent;

controlling the blood coagulation analyzer so as to emit light to the second measurement sample to detect light from the second measurement sample; and acquiring, based on the light detected from the second measurement sample, a fibrinogen concentration in the blood sample.

A eighth aspect of the present invention is a computer program product comprising:

a computer readable medium, and a software instructions, on the computer readable medium, for enabling a computer to perform predetermined operations, comprising:

controlling a blood coagulation analyzer so as to prepare a first measurement sample from a blood sample and a prothrombin time measurement reagent, a partial thromboplastin time measurement reagent, or an activated partial thromboplastin time measurement reagent;

controlling the blood coagulation analyzer so as to emit light to the first measurement sample to detect light from the measurement sample;

acquiring, based on the light detected from the first measurement sample, a derived fibrinogen concentration reflecting a fibrinogen concentration in the blood sample;

changing, depending on the derived fibrinogen concentration, a preparation condition of a second measurement sample prepared from the blood sample and a fibrinogen concentration measurement reagent;

controlling the blood coagulation analyzer so as to prepare, based on the changed preparation condition, a second measurement sample from the blood sample and a fibrinogen concentration measurement reagent;

controlling the blood coagulation analyzer so as to emit light to the second measurement sample to detect light from the second measurement sample; and acquiring, based on the light detected from the second measurement sample, a fibrinogen concentration in the blood sample.

A ninth aspect of the present invention is a computer program product comprising:

a computer readable medium, and a software instructions, on the computer readable medium, for enabling a computer to perform predetermined operations, comprising:

controlling a blood coagulation analyzer so as to prepare a measurement sample from a blood sample and a prothrombin time measurement reagent, a partial thromboplastin time measurement reagent, or an activated partial thromboplastin time measurement reagent;

controlling the blood coagulation analyzer so as to emit light to the prepared measurement sample to detect light transmitted through the measurement sample;

acquiring, based on the detected light, ratio information reflecting a ratio between a first value reflecting the intensity of the light transmitted through the measurement sample of a clotting reaction starting stage and a second value reflecting the intensity of the light transmitted through the measurement sample of a clotting reaction ending stage; and acquiring, based on the ratio information, a fibrinogen concentration in the blood sample.

BRIEF DESCRIPTION OF THE DRAWINGS

FIGS. 13(a)-13(c) are exemplary screen displays showing results of analysis by the blood coagulation analyzer;

DETAILED DESCRIPTION OF THE PREFERRED EMBODIMENTS

Figure 1:
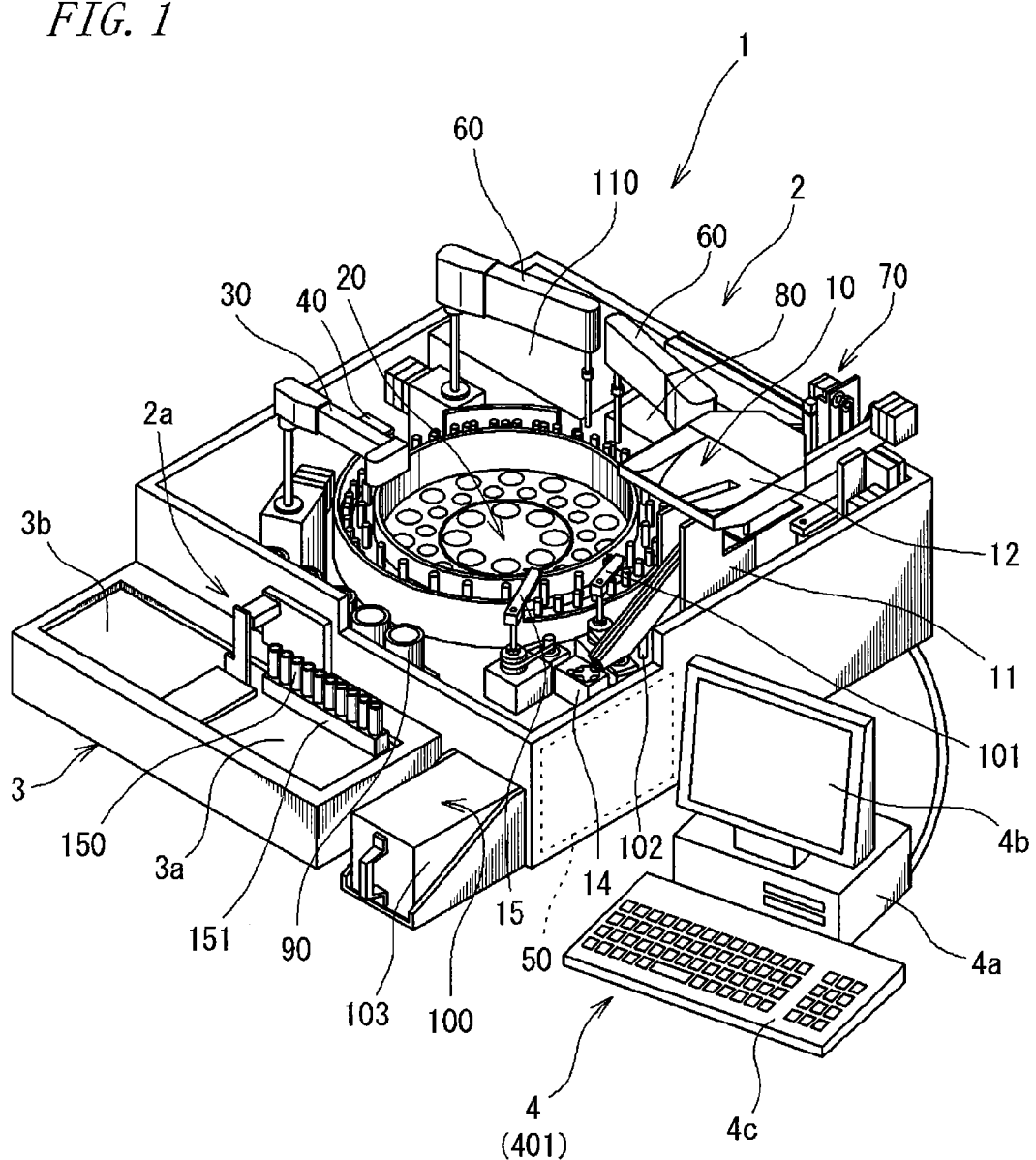
FIG. 1 is a perspective explanatory diagram illustrating the entire configuration of a blood coagulation analyzer according to an embodiment of the present invention.
Figure 2:
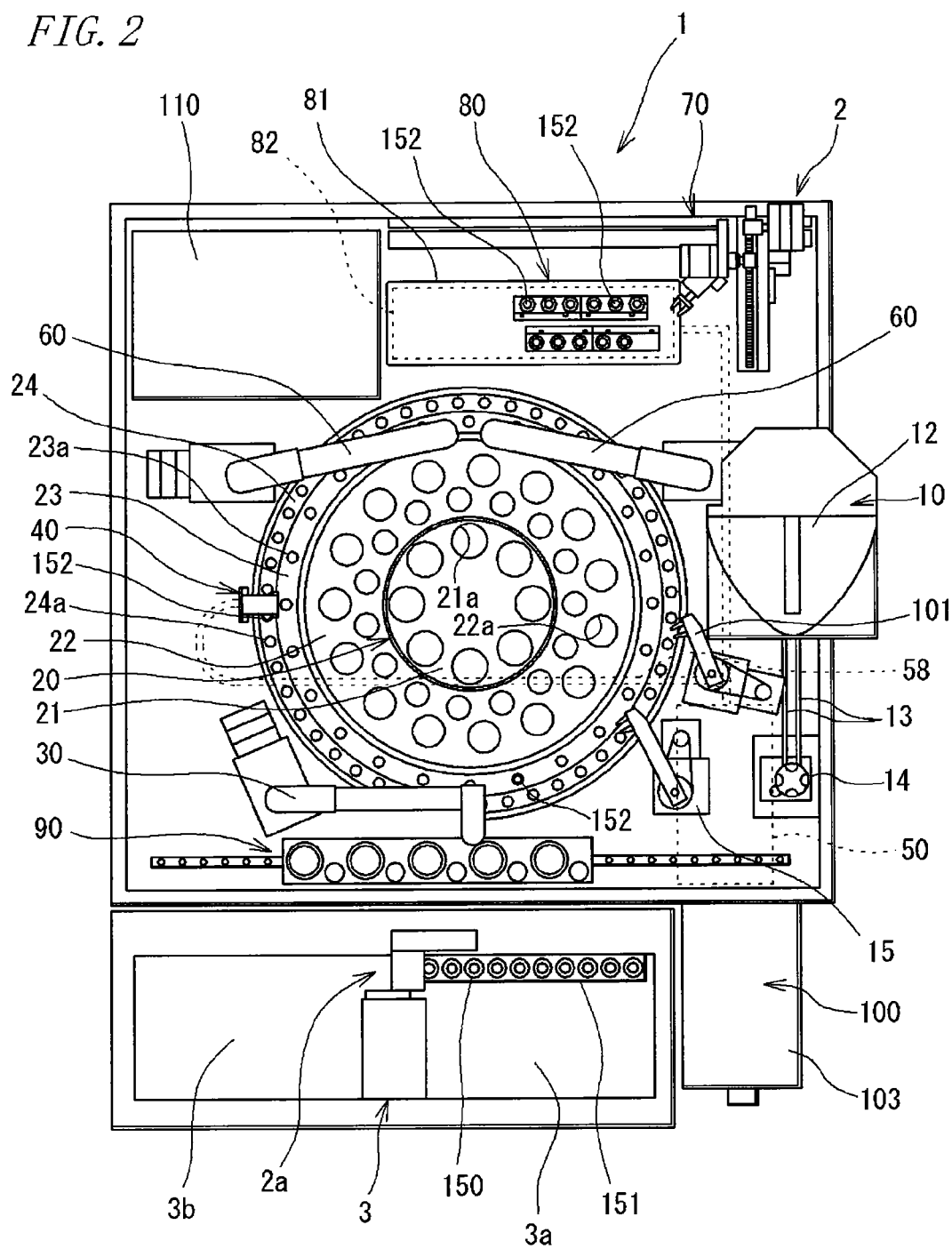
FIG. 2 is a top explanatory diagram illustrating a measurement apparatus (a measurement section and a carrying section) in the blood coagulation analyzer.

FIG. 1 is a perspective explanatory diagram illustrating the entire configuration of a blood coagulation analyzer 1 according to an embodiment of the present invention, and FIG. 2 is a top explanatory diagram illustrating a measurement section 2 and a carrying section 3 of the blood coagulation analyzer 1.

[Entire Configuration of Blood Coagulation Analyzer]

The blood coagulation analyzer 1 according to the present embodiment optically measures and analyzes, with regard to a specimen (blood sample), the amount and the activity level of a specific substance related to the clotting and fibrinolytic function. This analyzer 1 uses the clotting time method, the synthetic substrate method, and the immunoturbidimetric method to perform an optical measurement (main measurement) of the specimen. The present embodiment uses such a clotting time method that detects a plasma clotting process as a change of transmitted light. This method measures measurement items including PT (prothrombin time), PTT (partial thromboplastin time), APTT (activated partial thromboplastin time), Fbg (fibrinogen concentration), and LA (lupus anticoagulant). The synthetic substrate method measures measurement items including AT-III. The immunoturbidimetric method measures measurement items including D dimer and FDP. The blood coagulation analyzer 1 of the present embodiment also has a function to use the PT or APTT measurement result to compute a value corresponding to Fbg (derived fibrinogen concentration; hereinafter also referred to as a dFbg value).

As shown in FIG. 1, the analyzer 1 is mainly composed of: a measurement apparatus that has the measurement section 2 and the carrying section 3 provided at the front face-side of the measurement section 2; and a control apparatus 4 that is a data processing unit electrically connected to the measurement section 2. It is noted that, in the present embodiment, although the carrying section 3 is integrated with the measurement section 2 to constitute a part of the analyzer 1, this carrying section 3 also may be separated from the analyzer 1. For example, a large system including a plurality of analyzers may be configured so that no carrying section is provided in each analyzer and a large carrying line is connected to a plurality of analyzers.

[Configuration of Measurement Apparatus]

Figure 3:
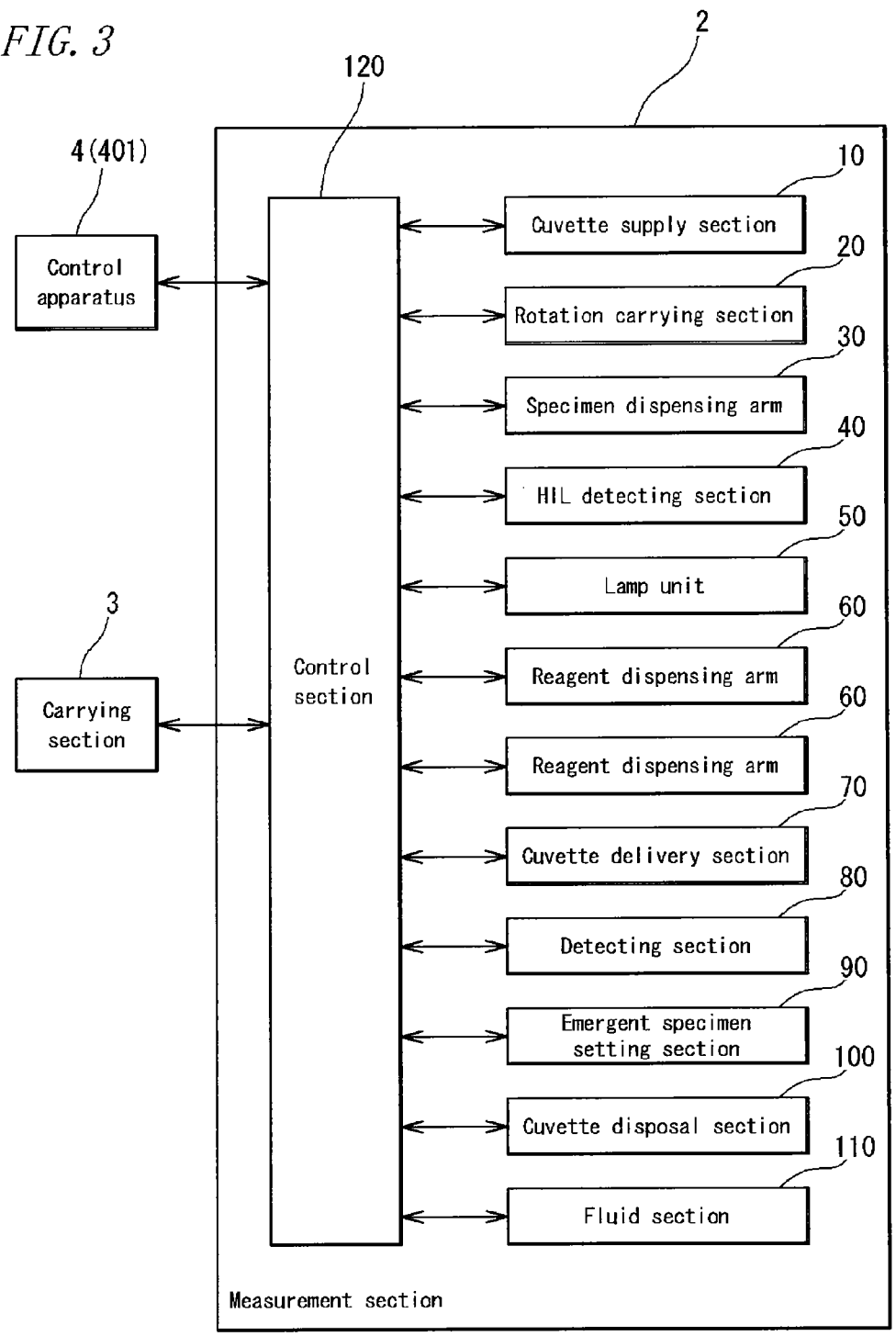
FIG. 3 is a block diagram illustrating the configuration of the measurement section in the blood coagulation analyzer.

The measurement section 2 of the measurement apparatus is configured so that a specimen supplied from the carrying section 3 is subjected to an optical measurement to thereby acquire the optical information regarding the supplied specimen (optical information). In the present embodiment, an optical measurement is carried out on the specimen dispensed from a test tube 150 placed in a rack 151 of the carrying section 3 to a cuvette (reaction container) 152 (see FIG. 2) in the measurement section 2. The measurement section 2 includes, as shown in FIG. 1 and FIG. 2, a cuvette supply section 10, a rotation carrying section 20, a specimen dispensing arm 30, an HIL detecting section 40, a lamp unit 50, two reagent dispensing arms 60, a cuvette delivery section 70, a detecting section 80, an emergent specimen setting section 90, a cuvette disposal section 100, a fluid section 110, and a control section 120 (FIG. 3). The control section 120 has a function to control the operations of the respective mechanisms in the measurement section 2 and the carrying section 3.

The cuvette supply section 10 is so configured as to sequentially supply to the rotation carrying section 20 a plurality of cuvettes 152 inputted by a user in a random way. This cuvette supply section 10 includes, as shown in FIG. 2, a hopper 12 that is attached via a bracket 11 (see FIG. 1) to the apparatus body; two guide plates 13 provided at the lower side of the hopper 12; a support stand 14 provided at the lower end of the two guide plates 13; and a supply catcher section 15 provided to have a predetermined interval from the support stand 14. The two guide plates 13 are arranged to be parallel to each other so as to have therebetween such an interval that is smaller than the diameter of the flange section of the cuvette 152 and that is larger than the diameter of the barrel section of the cuvette 152. The cuvette 152 is so configured, upon being supplied in the hopper 12, as to slip down to the support stand 14 while the flange section being engaged with the upper faces of the two guide plates 13. The support stand 14 has a function to deliver, in a rotating manner, the cuvette 152 slipped down the guide plates 13 to a position at which the cuvette 152 can be caught by the supply catcher section 15. Then, the supply catcher section 15 is provided to supply to the rotation carrying section 20 the cuvette 152 rotatingly delivered by the support stand 14.

The rotation carrying section 20 is provided to carry, in the rotating direction, the cuvette 152 supplied from the cuvette supply section 10 and a reagent container (not shown) containing therein reagent to be added to the specimen in the cuvette 152. This rotation carrying section 20 is composed, as shown in FIG. 2, of a circular reagent table 21, an annular-shaped reagent table 22 provided at the outer side of the circular reagent table 21, an annular-shaped secondary dispensing table 23 provided at the outer side of the annular-shaped reagent table 22; and an annular-shaped primary dispensing table 24 provided at the outer side of the annular-shaped secondary dispensing table 23. These primary dispensing table 24, secondary dispensing table 23, reagent table 21, and reagent table 22 are so configured as to be rotatable independently both in the clockwise direction and the counter-clockwise direction.

The reagent tables 21 and 22 include, as shown in FIG. 2, a plurality of hole sections 21a and 22a that are provided along the circumference direction to have a predetermined interval therebetween, respectively. The hole section 21a and 22a of the reagent tables 21 and 22 are provided to place a plurality of reagent containers (not shown) containing therein various reagents that are added when a measurement sample is prepared from a specimen. The primary dispensing table 24 and the secondary dispensing table 23 include a plurality of cylindrical-shaped retention sections 24a and 23a that are provided along the circumference direction to have a predetermined interval therebetween, respectively. The retention sections 24a and 23a are provided to retain the cuvette 152 supplied from the cuvette supply section 10. The cuvette 152 retained by the retention section 24a of the primary dispensing table 24 receives, during the primary dispensing processing, the specimen dispensed from the test tube 150 of the carrying section 3. The cuvette 152 retained by the retention section 23a of the secondary dispensing table 23 receives, during the secondary dispensing processing, the specimen dispensed from the cuvette 152 retained by the primary dispensing table 24. The retention section 24a includes a pair of small holes formed at positions opposing to each other on the side of the retention section 24a. The pair of small holes is provided to transmit the light emitted from a branched optical fiber 58 of the lamp unit 50 which will be described later.

The specimen dispensing arm 30 has a function to suck the specimen contained in the test tube 150 carried by the carrying section 3 to a suction position 2a and to dispense the sucked specimen into the cuvette 152 delivered to the rotation carrying section 20.

The HIL detecting section 40 is so configured as to acquire the optical information from a specimen in order to determine presence or absence and the concentration of interfering substance (chyle, hemoglobin, and bilirubin) in the specimen to which reagent is not added yet. Specifically, the HIL detecting section 40 determines the presence or absence and the concentration of interfering substance by using the four types of lights (405 nm, 575 nm, 660 nm, and 800 nm) of the five types of lights (340 nm, 405 nm, 575 nm, 660 nm, and 800 nm) emitted from the lamp unit 50 which will be described later. It is noted that light having a wavelength of 405 nm is light that is absorbed by any of chyle, hemoglobin, and bilirubin. In other words, optical information obtained by light having a wavelength of 405 nm is influenced by chyle, hemoglobin, and bilirubin. Light having a wavelength of 575 nm is light that is not substantially absorbed by bilirubin and that is absorbed by chyle and hemoglobin. In other words, optical information obtained by light having a wavelength of 575 nm is influenced by chyle and hemoglobin. Lights having wavelengths of 660 nm and 800 nm are lights that are not substantially absorbed by bilirubin and hemoglobin and that are absorbed by chyle. In other words, optical information obtained by lights having wavelengths of 660 nm and 800 nm is influenced by chyle. Chyle absorbs light in a range from a low wavelength region of 405 nm to a high wavelength region of 800 nm. Light having a wavelength of 660 nm is more absorbed by chyle than light having a wavelength of 800 nm. In other words, optical information obtained by light having a wavelength of 800 nm is less influenced by chyle than optical information obtained by light having a wavelength of 660 nm.

This acquisition by the HIL detecting section 40 of the optical information regarding a specimen is performed prior to the optical measurement by the detecting section 80 regarding the specimen (main measurement). The HIL detecting section 40 acquires, as shown in FIG. 2, optical information from the specimen in the cuvette 152 retained by a retention section 24a of the primary dispensing table 24.

In the present embodiment, the lamp unit 50 is provided, as shown in FIG. 2, to supply light that is used for the optical measurement performed by the HIL detecting section 40 and the detecting section 80. In other words, one lamp unit 50 is so configured as to be commonly used for the HIL detecting section 40 and the detecting section 80.

The reagent dispensing arm 60 is provided, as shown in FIG. 1 and FIG. 2, to dispense the reagent in a reagent container (not shown) placed in the rotation carrying section 20 to the cuvette 152 retained in the rotation carrying section 20 to thereby mix the reagent with the specimen in the cuvette 152. Thus, the reagent is added to the specimen for which the optical measurement by the HIL detecting section 40 is completed to thereby prepare a measurement sample. The cuvette delivery section 70 is provided to deliver the cuvette 152 between the rotation carrying section 20 and the detecting section 80. To the vicinity of a tip end of the reagent dispensing arm 60, there is attached a heating pipette that configures a heating apparatus having a reagent heating function.

The detecting section 80 has functions to heat the measurement sample prepared by adding the reagent to the specimen and to measure optical information from the measurement sample. This detecting section 80 includes, as shown in FIG. 2, a cuvette receiver 81 and a detector 82 provided at the lower side of the cuvette receiver 81.

Figure 5:
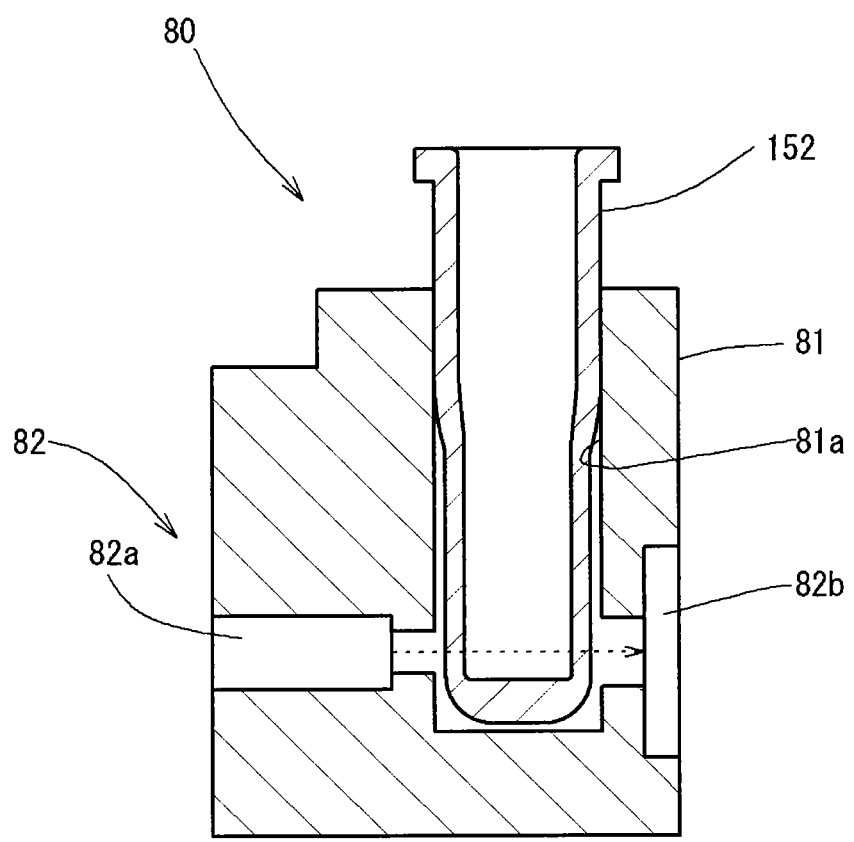
FIG. 5 is a cross-sectional view illustrating a detecting section in the blood coagulation analyzer.

FIG. 5 is a cross-sectional view of the detecting section 80. The cuvette receiver 81 has a plurality of insertion holes 81a. The cuvette 152 is inserted to the insertion hole 81a. The detector 82 has a light source 82a and a photoelectric conversion element 82b. Light that is emitted from the light source 82a and that is transmitted through the cuvette 152 (transmitted light) is received by the photoelectric conversion element 82b. The light source 82a may be a halogen lamp or LED. The photoelectric conversion element 82b may be a photodiode. It is noted that the cuvette receiver 81 also includes an insertion hole having a heating function (not shown).

The emergent specimen setting section 90 is provided, as shown in FIG. 1 and FIG. 2, for the analysis processing of an emergent specimen. This emergent specimen setting section 90 is configured so that an emergent specimen can interrupt the analysis processing of the specimen supplied from the carrying section 3. The cuvette disposal section 100 is provided to dispose the cuvette 152 in the rotation carrying section 20. The cuvette disposal section 100 is composed, as shown in FIG. 2, of a disposal catcher section 101, a disposal hole 102 (see FIG. 1) provided to have a predetermined interval from the disposal catcher section 101, and a disposal box 103 provided at the lower side of the disposal hole 102. The disposal catcher section 101 is provided to move the cuvette 152 in the rotation carrying section 20 to the disposal box 103 via the disposal hole 102 (see FIG. 1). The fluid section 110 is provided to supply, during the shutdown processing of the analyzer 1, liquid such as cleaning liquid to a nozzle provided in each dispensing arm.

FIG. 3 is a block diagram illustrating the configuration of the measurement section 2. The control section 120 is connected to the cuvette supply section 10, the rotation carrying section 20, the specimen dispensing arm 30, the HIL detecting section 40, the lamp unit 50, two the reagent dispensing arms 60, the cuvette delivery section 70, the detecting section 80, the emergent specimen setting section 90, the cuvette disposal section 100, and the fluid section 110 so that an electric signal can be communicated therebetween. The control section 120 is composed of CPU, ROM, RAM or the like. By allowing the CPU to execute a control program memorized in advance in the ROM, the operations of the above-described respective mechanisms are controlled to thereby allow the measurement section 2 to carry out a measurement operation or a maintenance operation for example.

The carrying section 3 of the measurement apparatus has, as shown in FIG. 1, a function, in order to supply a specimen to the measurement section 2, to carry the rack 151 containing therein a plurality of test tubes 150 (or ten test tubes 150 in the present embodiment) containing therein specimens to the suction position 2a of the measurement section 2. The carrying section 3 has a rack setting region 3a for setting the rack 151 containing therein the test tube 150 containing therein an unprocessed specimen and a rack storage region 3b for containing the rack 151 containing therein the test tube 150 containing therein a processed specimen.

[Configuration of Control Apparatus]

As shown in FIG. 1, the control apparatus 4 is composed of a personal computer 401 (PC) for example and includes a control section 4a, a display section 4b, and a keyboard 4c. The control section 4a has functions to control the operations of the measurement section 2 and the carrying section 3 and to analyze the optical information of the specimen obtained by the measurement section 2. This control section 4a is composed of CPU, ROM, or RAM for example. The display section 4b is provided to display the analysis result obtained by the control section 4a and to display the maintenance history for example of the analyzer 1.

Figure 4:
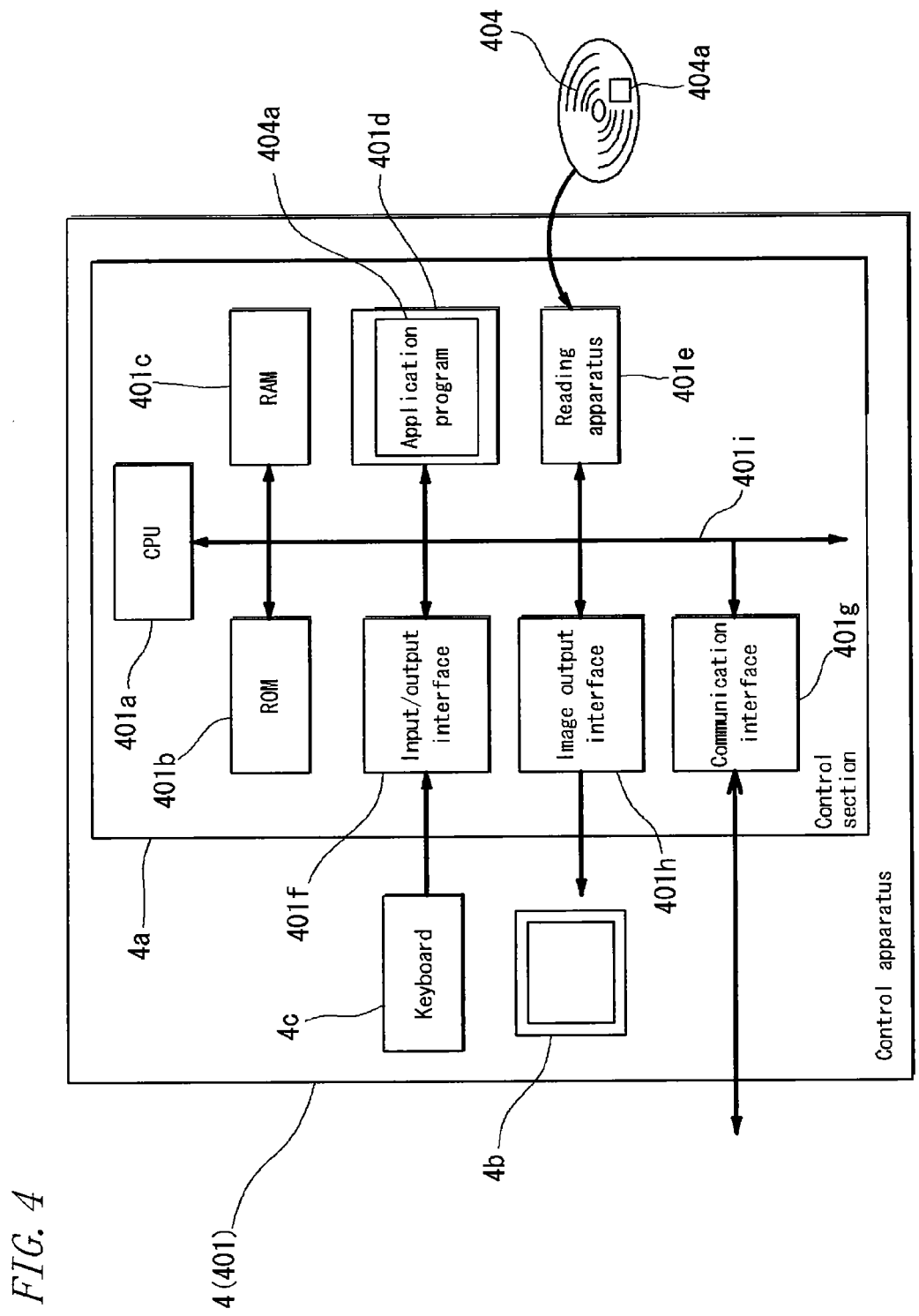
FIG. 4 is a block diagram illustrating a control apparatus in the blood coagulation analyzer.

FIG. 4 is a block diagram illustrating the control apparatus 4 in the analyzer 1. The control section 4a is mainly composed of: a CPU 401a, a ROM 401b, a RAM 401c, a hard disk 401d, a reading apparatus 401e, an input/output interface 401f, a communication interface 401g, and an image output interface 401h. The CPU 401a, The ROM 401b, the RAM 401c, the hard disk 401d, the reading apparatus 401e, the input/output interface 401f, the communication interface 401g, and the image output interface 401h are connected via a bus 401i.

The CPU 401a can execute a computer program memorized in the ROM 401b and a computer program loaded to the RAM 401c.

The ROM 401b is composed of a mask ROM, PROM, EPROM, and EEPROM for example. The ROM 401b records a computer program to be executed by the CPU 401a and the data to be used for the computer program for example.

The RAM 401c is composed of SRAM or DRAM for example. The RAM 401c is used to read a computer programs recorded in the ROM 401b and the hard disk 401d. The RAM 401c is also used as a working region of the CPU 401a when the computer programs are executed.

In the hard disk 401d, various computer programs such as an operating system and an application program 404a to be executed by the CPU 401a and data to be used to execute the computer programs are installed. As described later, an application program to analyze the measurement result such as PT and APTT and an application program to acquire dFbg from the measurement result are also installed in the hard disk 401d.

The reading apparatus 401e is composed of a flexible disk drive, a CD-ROM drive, or a DVD-ROM drive for example. The reading apparatus 401e can read a computer program or data recorded in the portable recording medium 404.

The input/output interface 401f is composed, for example, of a serial interface such as USB, IEEE1394 or RS-232C, a parallel interface such as SCSI, IDE or IEEE1284, or an analog interface comprising D/A converter or A/D converter. The keyboard 4C is connected to the input/output interface 401f. A user can use the keyboard 4c to input data to the computer 401.

The communication interface 401g is an Ethernet® interface for example. The computer 401 can realize data transmission to and reception from the measurement section 2 via the communication interface 401g, using a predetermined communication protocol.

The image output interface 401h is connected to the display section 4b comprising LCD or CRT for example. The image output interface 401h is so configured as to output to the display section 4b a video signal depending on the image data given from the CPU 401a. The display section 4b displays an image (screen) in accordance with the inputted video signal.

[Analysis Operation Procedure]

Next, the following section will describe, via three examples, an analysis operation of a specimen by the blood coagulation analyzer 1. It is noted that an item to be measured is a plasma PT (prothrombin time).

First Example

Figure 6:
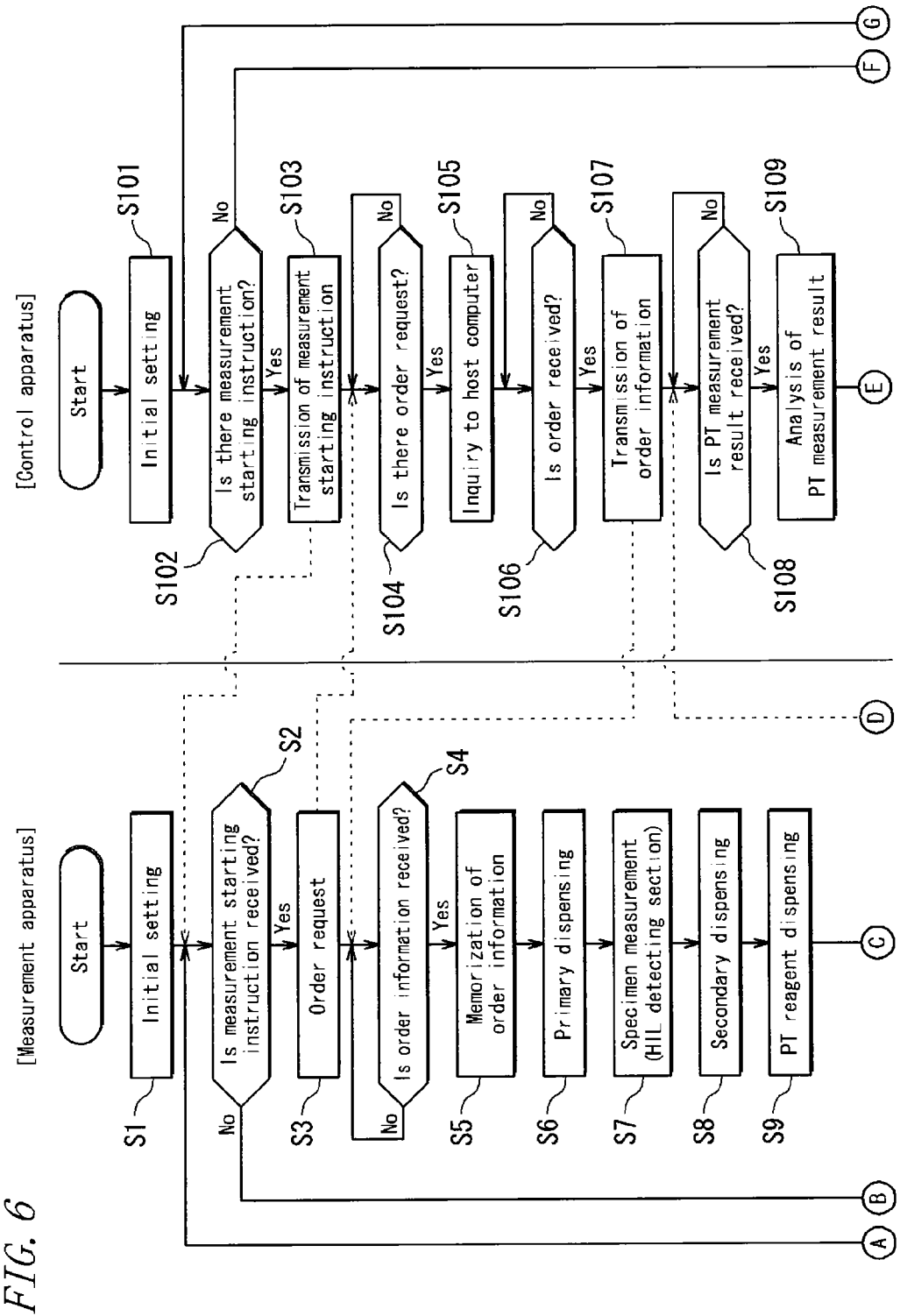
FIG. 6 is the first half of the flowchart showing the first example of an analysis operation procedure by the blood coagulation analyzer.
Figure 7:
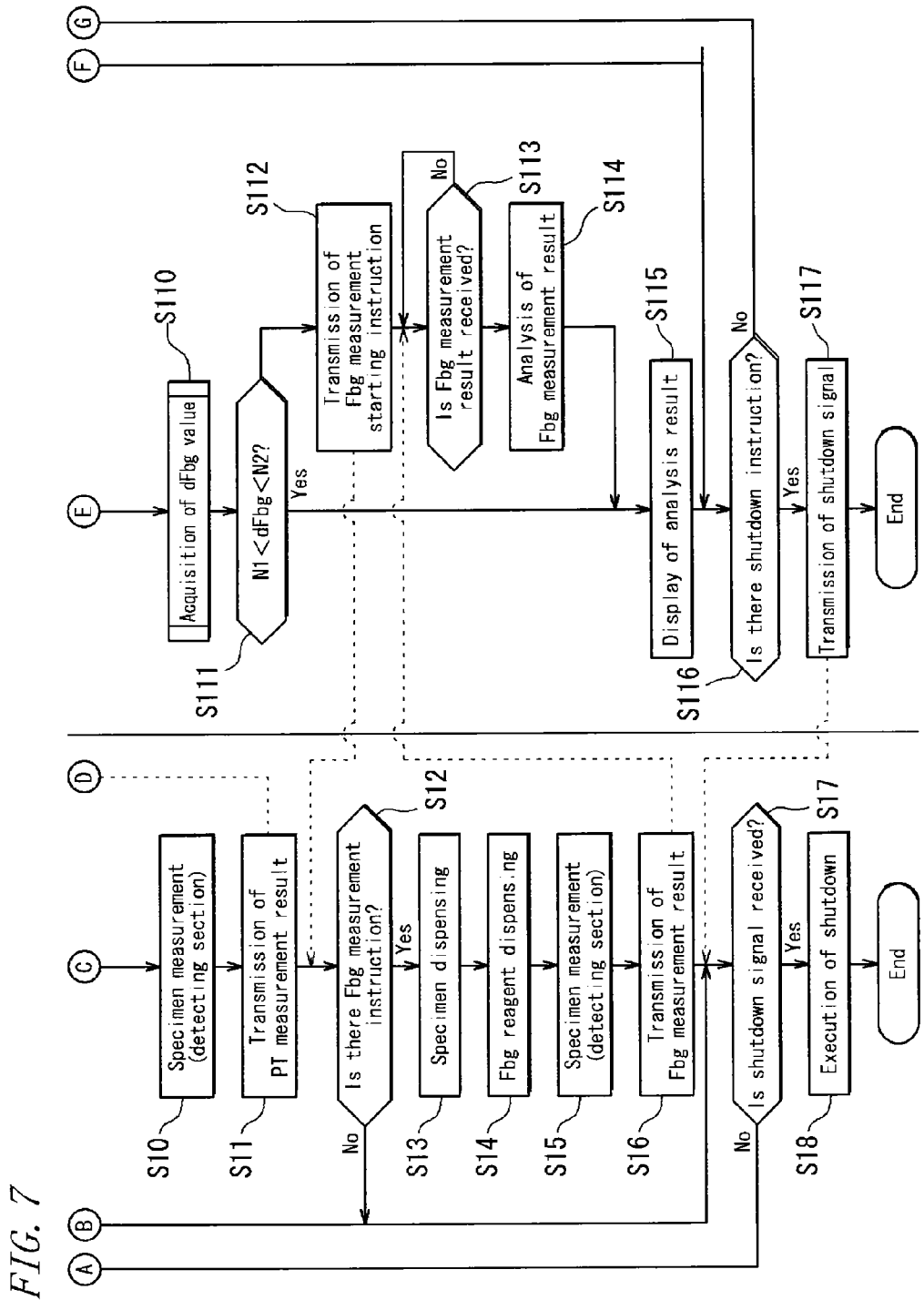
FIG. 7 is the second half of the flowchart showing the first example of an analysis operation procedure according to the blood coagulation analyzer.

FIG. 6 and FIG. 7 show a flowchart illustrating the first example of the analysis operation procedure by the blood coagulation analyzer 1. FIG. 6 shows the first half and FIG. 7 shows the second half of the flowchart. It is noted that A to G in FIG. 6 are connected to A to G in FIG. 7, respectively.

First, the respective power source of the measurement apparatus and the control apparatus 4 of the analyzer 1 shown in FIG. 1 is turned ON to thereby initialize the analyzer 1 (steps S1 and S101). This consequently provides an operation to return a mechanism for moving the cuvette 152 and the respective dispensing arms to initial positions and the initialization of software memorized in the control section 4a of the control apparatus 4 for example.

Next, in Step S102, it is determined by the control section 4a whether a measurement starting instruction is accepted or not. When the control section 4a determines that the measurement starting instruction is accepted (Yes), the processing proceeds to Step S103. When the control section 4a determines that the measurement starting instruction is not accepted (No), the processing proceeds to Step S116. Then, in Step S103, the control section 4a sends a measurement starting signal to the control section 120 of the measurement apparatus.

Next, in Step S2, the control section 120 of the measurement apparatus determines whether the measurement starting signal is received or not. When the control section 120 determines that the measurement starting signal is received (Yes), the processing proceeds to Step S3. When the control section 120 determines that the measurement starting signal is not received (No), the processing proceeds to Step S17.

Next, in Step S3, the control section 120 of the measurement apparatus requests an order to the control section 4a of the control apparatus 4. In other words, in the measurement apparatus, there are read bar codes that record therein information for identifying the rack 151 on the carrying section 3 and information for identifying the test tube 150. This read information is sent by the control section 120 to the control apparatus 4.

Next, in Step S104, the control section 4a of the control apparatus 4 determines whether the order request from the measurement apparatus is accepted or not. When the control section 4a determines that the order request is accepted (Yes), the processing proceeds to Step S105.

The control section 4a inquires of the host computer about order information regarding the order request (Step S105). Thereafter, the control section 4a determines whether order information as a response from the host computer is received or not (Step S106). Then, when the control section 4a determines that the order information is received, the control section 4a sends the order information to the control section 120 of the measurement apparatus (Step S107).

Next, in Step S4, the control section 120 of the measurement apparatus determines whether the order information is received or not. When the control section 120 determines that the order information is received, the memory section such as RAM memorizes the order information in Step S5.

Next, in Step S6, the specimen dispensing arm 30 sucks a predetermined amount of a specimen from the test tube (sample container) 150. Then, the specimen dispensing arm 30 is moved to the upper side of the cuvette 152 retained by the primary dispensing table 24 of the rotation carrying section 20. Thereafter, the specimen is discharged from the specimen dispensing arm 30 into the cuvette (storage container) 152 of the primary dispensing table 24 to thereby perform a primary dispensing of the specimen into the cuvette 152.

Then, the primary dispensing table 24 is rotated to carry the cuvette 152 in which the specimen is dispensed to a position at which the measurement by the HIL detecting section 40 is possible. In Step S7, the optical measurement of the specimen is performed by the HIL detecting section 40.

Next, in Step S8, the specimen dispensing arm 30 sucks the predetermined amount of the specimen from the cuvette 152 retained by the retention section 24a of the primary dispensing table 24. Thereafter, the predetermined amount of the specimen is discharged from the specimen dispensing arm 30 to a plurality of cuvettes (reaction containers) 152 of the secondary dispensing table 23, to thereby perform a secondary dispensing processing.

Next, in Step S9, the reagent dispensing arm 60 is driven to add the PT measurement reagent in a reagent container (not shown) placed in the reagent tables 21 and 22 to the specimen in the cuvette 152 of the secondary dispensing table 23. Thus, the measurement sample is prepared. Then, the cuvette delivery section 70 is used to move the cuvette 152 in the secondary dispensing table 23 containing therein the measurement sample to an insertion hole 81a of the cuvette receiver 81 of the detecting section 80.

It is noted that the specimen dispensing arm 30 and the reagent dispensing arm 60 for example configure a sample preparation section that mixes the specimen with the PT measurement reagent to thereby prepare a measurement sample.

Next, in Step S10, the detector 82 of the detecting section 80 subjects the measurement sample in the cuvette 152 to an optical PT measurement. In this PT measurement, light is emitted from the light source 82a and the light transmitted through the measurement sample in the cuvette 152 is received by the photoelectric conversion element 82b and is converted to an electric signal depending on the transmitted light amount (transmitted light intensity). The electric signal is converted by an A/D converter (not shown) to a digital signal. The measurement result is acquired as data in which the transmitted light intensity for each predetermined time is associated with the time at which each transmitted light intensity is measured.

Next, in Step S11, the control section 120 of the measurement apparatus sends the PT measurement result to the control apparatus 4.

Next, in Step S108, the control section 4a of the control apparatus 4 determines whether the PT measurement result is received or not. When the control section 4a determines that the PT measurement result is received (Yes), the PT measurement result is analyzed in Step S109.

Figure 14:
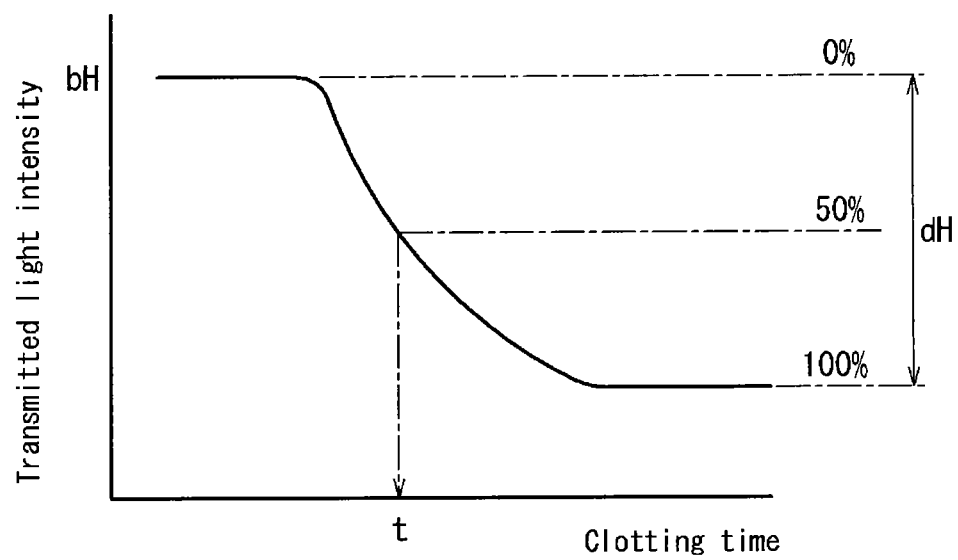
FIG. 14 is a schematic view illustrating a clotting reaction curve by the blood coagulation analyzer.

First, the control section 4a generates, based on the data acquired through the PT measurement, a clotting reaction curve showing a change in the transmitted light intensity with time passage. FIG. 14 is a graph illustrating this clotting reaction curve. According to the clotting reaction curve, there is almost no change in the transmitted light intensity at the start of the measurement immediately after the addition of the reagent. However, with the promotion of clotting thereafter, the measurement sample becomes cloudy and a rapid decrease is seen in the transmitted light intensity. Then, when the clotting reaction almost ends, a change in the transmitted light intensity decreases and the transmitted light intensity is substantially fixed thereafter.

The control section 4a detects, based on the clotting reaction curve, a time point at which a clotting reaction starts and a time point at which a clotting reaction ends. Then, it is assumed that the transmitted light intensity at the start of the clotting reaction (clotting reaction starting level) is 0% and the transmitted light intensity at the end of the clotting reaction (clotting reaction completion level) is 100%. Then, the time t at which a predetermined detection percent (e.g., 50%) is reached is calculated from the clotting reaction curve and this time t is acquired as PT. It is noted that the clotting reaction starting level is the maximum transmitted light intensity within a predetermined time (e.g., 60 seconds) from the addition of the reagent. The clotting reaction completion level is the transmitted light intensity at a time point that is after the time point at which the clotting reaction starting level is recognized and that is at a time point at which a decrease amount of the transmitted light intensity per a predetermined time is a predetermined value or lower.

It is noted that the clotting reaction starting level may be a transmitted light intensity detected at a stage at which a clotting reaction starts. The stage at which a clotting reaction starts includes not only a time point at which a clotting reaction starts but also all time zones within which transmitted light having the similar light intensity to the light intensity of transmitted light detected at a point at which a clotting reaction starts can be detected (e.g., an arbitrary time point prior to the start of a clotting reaction, a time at which the detection of transmitted light by the detecting section 80 is started, a time point immediately after the start of a clotting reaction). The clotting reaction completion level may be a transmitted light intensity detected at a stage at which a clotting reaction ends. The stage at which a clotting reaction ends includes not only a time point at which a clotting reaction ends but also all time zones within which transmitted light having the similar light intensity to the light intensity of transmitted light detected at a point at which a clotting reaction ends can be detected (e.g., a time point immediately before the end of a clotting reaction, an arbitrary time point after the end of a clotting reaction).

Figure 8:
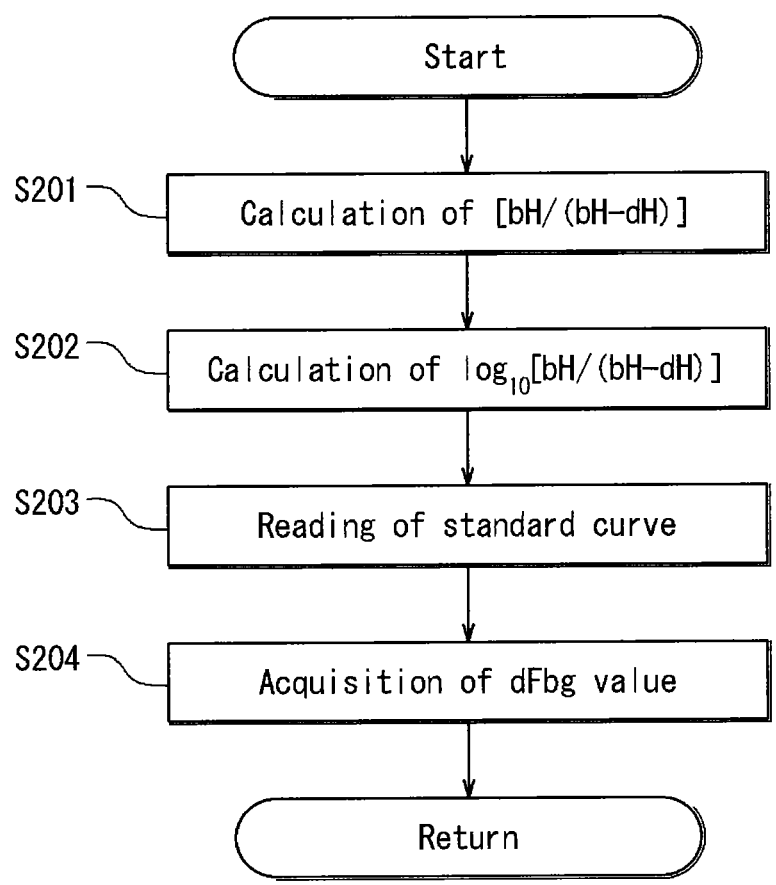
FIG. 8 is a flowchart illustrating the dFbg acquisition procedure in the analysis operation by the blood coagulation analyzer.

Next, in Step S110, the control section 4a performs a processing to acquire a dFbg value (derived fibrinogen concentration). FIG. 8 is a flowchart illustrating a processing procedure for acquiring a dFbg value.

First, in Step S201, the control section 4a uses, as shown in FIG. 14, the transmitted light intensity bH at the clotting reaction starting level and the change amount dH of the transmitted light intensity from the start of the clotting reaction to the end of the clotting reaction to calculate, by the following formula (1), the ratio B between the transmitted light intensity at the start of the clotting reaction and the transmitted light intensity at the end of the clotting reaction.

$$\text{Ratio: } B = bH/(bH - dH) \tag{1}$$

Here, (bH−dH) corresponds to the transmitted light intensity at the end of the clotting reaction.

Next, in Step S202, the control section 4a calculates the ratio information A by the following formula (2).

$$\text{Ratio information: } A = \log_{10} B \tag{2}$$

Next, in Step S203, the control section 4a reads out the standard curve memorized in the hard disk 401d to the RAM 401c. This standard curve shows the correlation between the ratio information A and the fibrinogen concentration and is prepared using a standard sample in advance. Then, in Step S204, the ratio information A is applied to the standard curve to thereby acquire the fibrinogen concentration. This fibrinogen concentration is assumed as a dFbg value (the first value).

Next, in Step S111 of FIG. 7, the control section 4a of the control apparatus 4 determines whether the dFbg value is within a predetermined range or not. In other words, it is determined whether the dFbg value satisfies the condition of N1<dFbg<N2. N1 and N2 are boundary values for determining whether or not an Fbg measurement is performed to measure a fibrinogen concentration in the blood sample using an exclusive reagent for measuring a fibrinogen concentration. N1 and N2 can be set by the user of the analyzer 1 depending on a test configuration for example.

Then, when the control section 4a determines that the dFbg value is within the predetermined range (Yes), the processing proceeds to Step S115. When the control section 4a determines that the dFbg value is not within the predetermined range (No), the processing proceeds to Step S112.

In Step S112, the control section 4a sends an Fbg measurement starting signal for starting an Fbg measurement to the measurement apparatus.

Next, in Step S12, the control section 120 of the measurement apparatus determines whether the Fbg measurement starting signal is received or not. When the control section 120 determines that the Fbg measurement starting signal is received (Yes), the processing proceeds to Step S13. When the control section 120 determines that the Fbg measurement starting signal is not received (No), the processing proceeds to Step S17.

Next, in Step S13, the specimen dispensing arm 30 sucks the predetermined amount of the specimen from the cuvette (storage container) 152 retained by the retention section 24a of the primary dispensing table 24. Thereafter, the predetermined amount of the specimen is discharged from the specimen dispensing arm 30 into the cuvette (reaction container) 152 of the secondary dispensing table 23 to thereby perform a dispensing processing for Fbg measurement.

Next, in Step S14, the reagent dispensing arm 60 adds the Fbg measurement reagent in a reagent container (not shown) placed on the reagent tables 21 and 22 to the specimen in the cuvette 152 of the secondary dispensing table 23. Thus, a measurement sample is prepared. Then, the cuvette delivery section 70 moves the cuvette 152 in the secondary dispensing table 23 containing therein the measurement sample to the insertion hole 81a of the cuvette receiver 81 of the detecting section 80.

Next, in Step S15, the measurement sample in the cuvette 152 is subjected to an optical Fbg measurement in the detector 82 of the detecting section 80. In the Fbg measurement, light is emitted from the light source 82a and the light transmitted through the measurement sample in the cuvette 152 is received by the photoelectric conversion element 82b and is converted to an electric signal depending on the transmitted light intensity thereof. The electric signal is converted by an A/D converter (not shown) to a digital signal. The measurement result is acquired as data in which the transmitted light intensity at each predetermined time is associated with each time at which the transmitted light intensity is measured. It is noted that the insertion hole 81a of the cuvette receiver 81 to which the cuvette 152 is inserted during Fbg measurement may be the same insertion hole as the insertion hole 81a to which the cuvette 152 is inserted during PT measurement or a different insertion hole.

Next, in Step S16, the control section 120 of the measurement apparatus sends the Fbg measurement result to the control apparatus 4.

Next, in Step S113, the control section 4a of the control apparatus 4 determines whether the Fbg measurement result is received or not. When the control section 4a determines that the Fbg measurement result is received (Yes), the Fbg measurement result is analyzed in Step S114.

This analysis of the Fbg measurement result is performed in substantially the same manner as that of the analysis of a PT measurement result. In other words, the control section 4a generates, based on the data acquired through the Fbg measurement, a clotting reaction curve showing a change in the transmitted light intensity with time passage. Then, based on the clotting reaction curve, a time (clotting time) at which a predetermined detection percent (for example 50%) is reached is calculated when the transmitted light intensity at the start of the clotting reaction is assumed as 0% and the transmitted light intensity at the end of the clotting reaction is assumed as 100%.

Then, the clotting time is applied to the standard curve that is prepared in advance using the standard sample and that is memorized in the hard disk 401d of the control section 4a to thereby calculate Fbg.

Next, in Step S115, the control section 4a causes the display section 4b to display the analysis result, in other words, PT and dFbg values and causes, when an Fbg measurement is performed, the display section 4b to display the Fbg. FIG. 13(a) shows an example of the display contents.

This measurement result shows the analysis result in a tabular form including columns for [PT] and [Fbg] as measurement items. The column for [PT] includes columns for [PTsec] (prothrombin time (second)) and [dFbg]. The column for [Fbg] further includes columns for [Fbgsec] (clotting time (second)) and [Fbg].

In FIG. 13(a), the specimen number 10001 has a dFbg value of 500 (mg/dL). This value is within a predetermined range (e.g., N1=150<dFbg<N2=600). Thus, no Fbg measurement is performed and the column for Fbg is left blank.

On the other hand, the specimen number 10002 has a dFbg value of 650 (mg/dL) which exceeds a predetermined range (N2=600<dFbg). The specimen number 10003 has a dFbg value of 120 (mg/dL) which is below a predetermined range (dFbg<N1=150). Thus, in these cases, the Fbg measurement using Fbg measurement reagent is performed and the analysis result acquired through the Fbg measurement is also displayed.

It is noted that, in FIG. 13(a), when an Fbg measurement is performed (specimen numbers of 10002 and 10003), the display of the dFbg value also may be omitted.

Next, in Step S116 of FIG. 7, the control section 4a determines whether a shutdown instruction is accepted or not. When the control section 4a determines that a shutdown instruction is accepted (Yes), the processing proceeds to Step S117. When the control section 4a determines that a shutdown instruction is not accepted (No), the processing proceeds to Step S102.

Next, in Step S117, a shutdown signal is sent from the control section 4a to the control section 120 of the measurement apparatus.

Next, in Step S17, the control section 120 of the measurement apparatus determines whether a shutdown signal is received or not. When the control section 120 determines that a shutdown signal is received (Yes), the processing proceeds to Step S18. When the control section 120 determines that a shutdown signal is not received (No), the processing returns to Step S2.

Then, in Step S18, the control section 120 shuts down the measurement apparatus, thereby completing the processing.

Second Example

Next, the following section will describe the second example of the analysis operation procedure of the blood coagulation analyzer 1.

Figure 9:
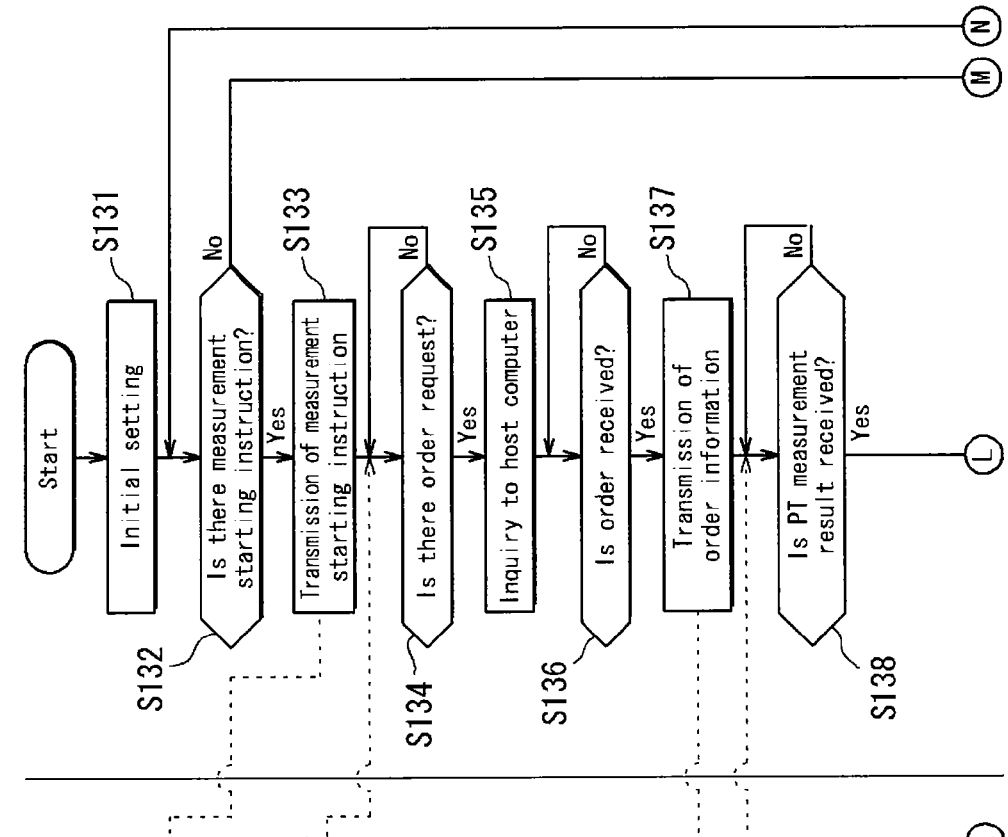
FIG. 9 is the first half of the flowchart showing the second example of an analysis operation procedure by the blood coagulation analyzer.
Figure 9:
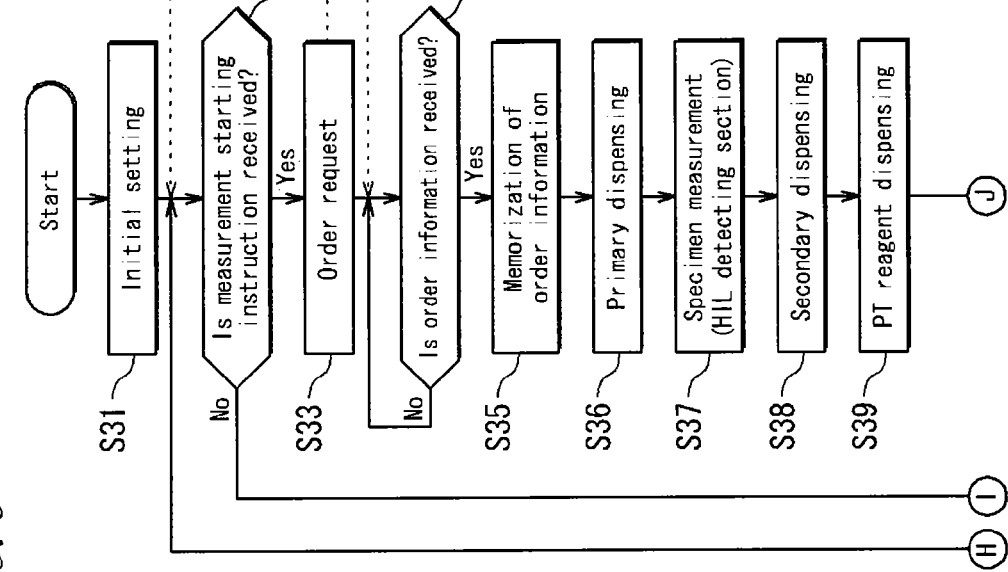
Figure 10:
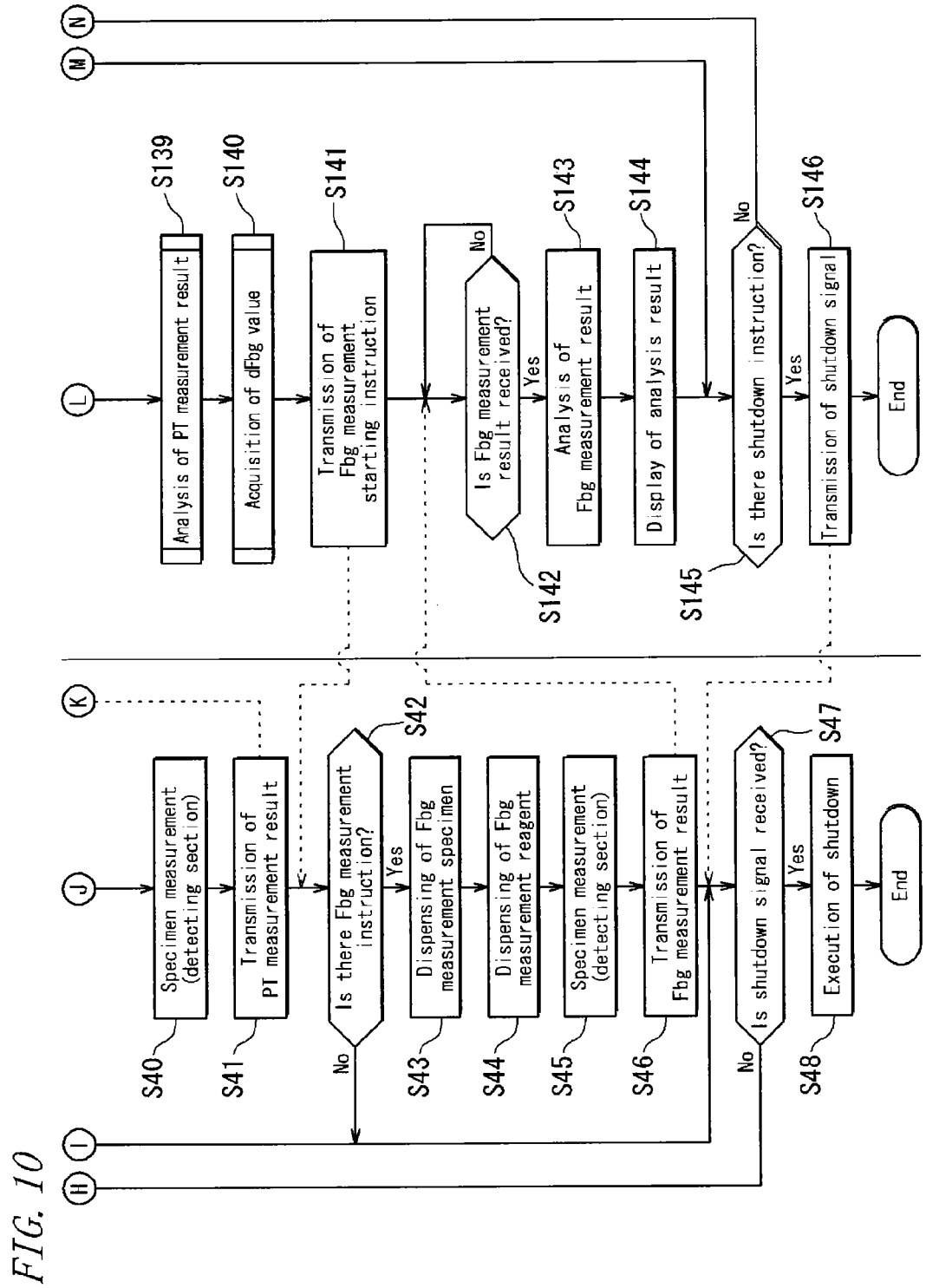
FIG. 10 is the second half of the flowchart showing the second example of an analysis operation procedure by the blood coagulation analyzer.

FIG. 9 to FIG. 10 show a flowchart illustrating the second example of the analysis operation procedure by the blood coagulation analyzer 1. FIG. 9 shows the first half and FIG. 10 shows the second half of the flowchart. It is noted that H to N in FIG. 9 are connected to H to N in FIG. 10, respectively.

The analysis operation procedure of the flowchart in FIG. 9 and FIG. 10 is different from that shown in FIG. 6 to FIG. 7 in that predetermined condition judgments are performed in Steps S43 and S44 in the measurement apparatus (see FIG. 11 and FIG. 12) and Steps S140 and S141 in the control apparatus 4 allow a dFbg value acquisition to be always followed by an instruction for starting an Fbg measurement. The following section will describe the flowchart in FIG. 9 to FIG. 10 mainly with regard to the differences from FIG. 6 to FIG. 7.

The processings from Step S31 to Step S41 in the measurement apparatus and the processings from Step S131 to Step S140 in the control apparatus 4 are performed in the same manners as those of Step S1 to Step S11 and those of Step S101 to Step S110, respectively, described with reference to FIG. 6 to FIG. 7.

The control section 4a of the control apparatus 4 calculates, in Step S140, a dFbg value by computation. Thereafter, the control section 4a sends, in Step S141, an Fbg measurement starting instruction signal to the measurement apparatus.

The control section 120 of the measurement apparatus determines, in Step S42, whether the Fbg measurement starting instruction signal is received or not. When the control section 120 determines that the Fbg measurement starting instruction signal is received, the processing proceeds to Step S43. When the control section 120 determines that the Fbg measurement starting instruction signal is not received, the processing proceeds to Step S47.

Figure 11:
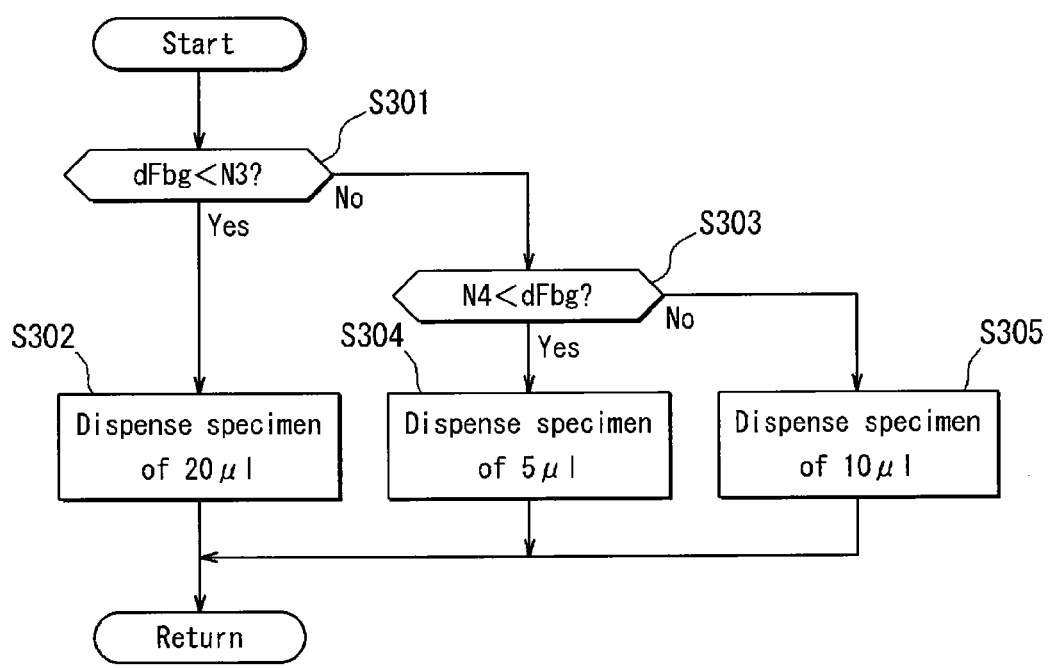
FIG. 11 is a flowchart illustrating a procedure of a specimen dispensing processing for an Fbg measurement in the analysis operation by the blood coagulation analyzer.

In Step S43, in the measurement apparatus, the Fbg measurement specimen is dispensed. FIG. 11 is a flowchart illustrating the procedure of the operation for dispensing an Fbg measurement specimen.

First, in Step S301, the control section 120 of the measurement apparatus determines whether the dFbg value is smaller than a predetermined threshold value N3 or not. This threshold value N3 and a threshold value N4 which will be described later are boundary values that are used to determine the measurement conditions for Fbg measurement and that are set in the blood coagulation analyzer 1 in advance in contrast with the above-described threshold values N1 and N2 that can be set by a user.

When the control section 120 determines that the dFbg value is smaller than the predetermined threshold value N3, the processing proceeds to Step S302. When the control section 120 determines that the dFbg value is equal to or higher than the predetermined threshold value N3, the processing proceeds to Step S303.

In Step S302, a specimen of 20 µl, which is in a higher amount than a standard amount (10 µl), is dispensed into the cuvette 152. This is for the reason that, when the dFbg value is smaller than the predetermined threshold value N3, the Fbg in the actual specimen is also considered to be low and thus the dilution degree of the measurement sample used for Fbg measurement is reduced in advance.

In Step S303, the control section 120 further determines whether the dFbg value is larger than the predetermined threshold value N4 or not. When the control section 120 determines that the dFbg value is larger than the predetermined threshold value N4, the processing proceeds to Step S304. When the control section 120 determines that the dFbg value is equal to or lower than the predetermined threshold value N4, then the processing proceeds to Step S305.

In Step S304, the specimen of 5 µl, which is in a lower amount than the standard amount, is dispensed into the cuvette 152. This is for the reason that, when the dFbg value is larger than the predetermined threshold value N4, the Fbg in the actual specimen is also considered to be high and thus the dilution degree of the measurement sample used for Fbg measurement is increased in advance.

In Step S305, the dFbg value is between the predetermined threshold value N3 and the threshold value N4. Thus, the specimen in the standard amount of 10 µL is dispensed to the cuvette 152. Then, after Steps S302, S304, and S305, the processing proceeds to Step S44 of FIG. 10.

Figure 12:
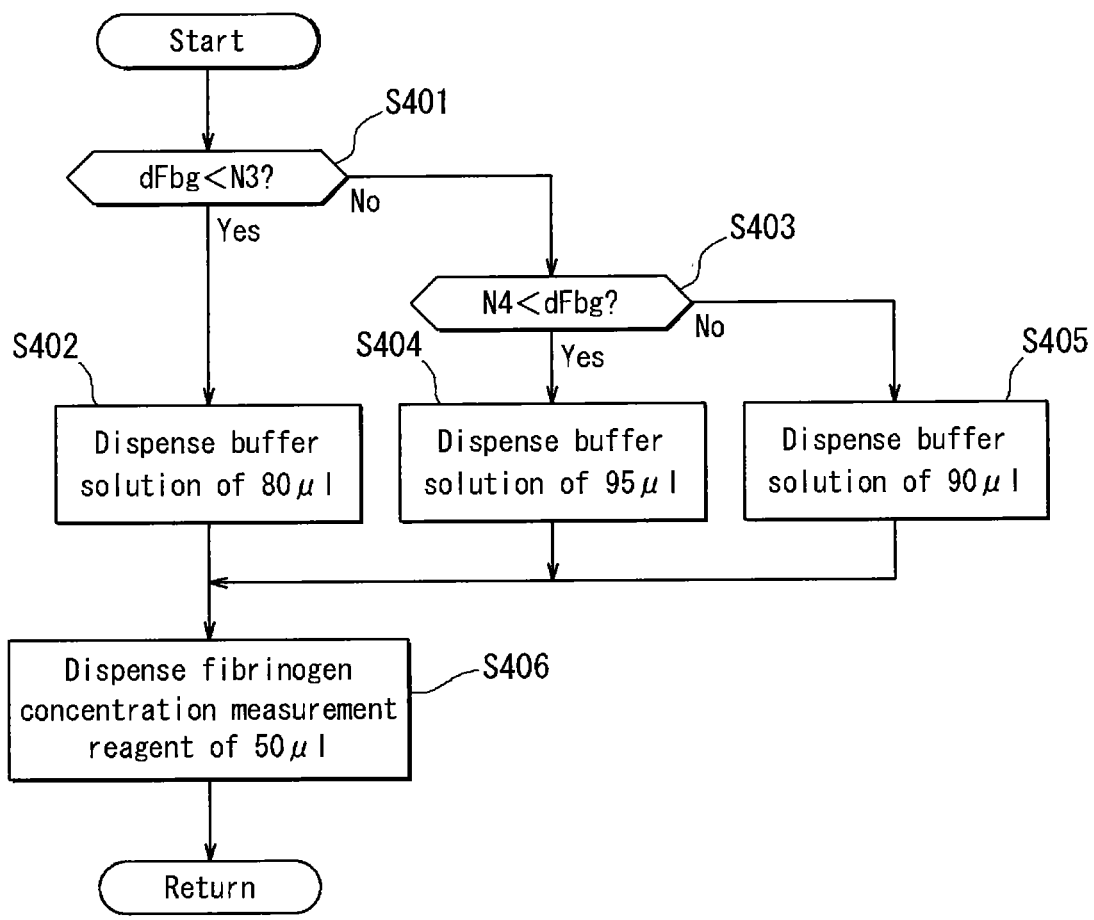
FIG. 12 is a flowchart illustrating a procedure of a reagent dispensing processing for an Fbg measurement in the analysis operation by the blood coagulation analyzer.

Next, in Step S44, an Fbg measurement reagent is dispensed. FIG. 12 is a flowchart illustrating the procedure of the operation for dispensing an Fbg measurement reagent.

First, in Step S401, the control section 120 of the measurement apparatus determines whether the dFbg value is smaller than the predetermined threshold value N3 or not. When the control section 120 determines that the dFbg value is smaller than the predetermined threshold value N3, the processing proceeds to Step S402. When the control section 120 determines that the dFbg value is equal to or larger than the predetermined threshold value N3, the processing proceeds to Step S403.

In Step S402, buffer solution (diluted solution) in an amount of 80 µl smaller than a standard amount (90 µl) is dispensed into the cuvette 152. Since 20 µl of specimen is already dispensed to the cuvette 152 (Step S302 of FIG. 11), five-times-diluted specimen of 100 µl is prepared.

In Step S403, the control section 120 determines whether the dFbg value is larger than the predetermined threshold value N4 or not. Then, when the control section 120 determines that the dFbg value is larger than the predetermined threshold value N4, the processing proceeds to Step S404. When the control section 120 determines that the dFbg value is equal to or smaller than the predetermined threshold value N4, the processing proceeds to Step S405.

In Step S404, buffer solution of 95 µl larger than the standard amount is dispensed to the cuvette 152. Since 5 µl of specimen is already dispensed to the cuvette 152 (Step S304 of FIG. 11), twenty-times-diluted specimen of 100 µl is prepared.

In Step S405, the dFbg value is equal to or larger than the predetermined threshold value N3 and is equal to or smaller than the predetermined threshold value N4. Thus, the buffer solution in the standard amount of 90 µL is dispensed to the cuvette 152. Since 10 µl of specimen is already dispensed in this cuvette 152 (Step S305 of FIG. 11), ten-times-diluted specimen of 100 µl is prepared.

After Step S402, S404, or S405, in Step S406, the Fbg measurement reagent of 50 µl is dispensed. Thus, the total of 150 µl of the measurement sample is prepared. Thereafter, the processing proceeds to Step S45 of FIG. 10. It is noted that buffer solution may be Owren's Veronal buffer solution (produced by SYSMEX CORPORATION) and Fbg measurement reagent may be thrombin reagent (produced by SYSMEX CORPORATION).

The processings after Step S45 in the measurement apparatus and the processings after Step S142 in the control apparatus 4 are the same as the processings described with reference to FIG. 6 to FIG. 7.

FIG. 13(b) illustrates a display example of an analysis result by the analysis operation procedure of the second example. In this table, all specimens are subjected to Fbg measurement. The specimen number 10003 has the dFbg value exceeding a predetermined range (e.g., N3=50<dFbg<N4=700), which is shown by a symbol ">" in the column for [dFbg]. When the dFbg value exceeds the predetermined range, the measurement sample in the Fbg measurement has a dilution degree higher than a standard degree. Thus, this is shown by a symbol "!" in the column for [Fbgsec].

Similarly, the specimen number 10004 has the dFbg value below the predetermined range. Thus, this is shown by a symbol "<" in the column for [dFbg]. In this case, the measurement sample in the Fbg measurement has a dilution degree lower than the standard degree. Thus, this is shown by the symbol "!" in the column for [Fbgsec].

Third Example

Although the analysis operation procedure by the blood coagulation analyzer 1 has been described with regard to the first example and the second example, another configuration is also possible where these two examples are combined. In other words, in the flowchart shown in FIG. 7, the specimen dispensing operation in Step S13 and the reagent dispensing operation in Step S14 also can be substituted with Step S43 and Step S44 of FIG. 10. In this case, in Step S111 of FIG. 7, it is determined whether the dFbg value satisfies the condition of the predetermined range (N1<dFbg<N2) or not. When the dFbg value does not satisfy the condition of the predetermined range (N1<dFbg<N2), in Step S13, the dispensing amount of the specimen is determined by the conditional judgment as shown in FIG. 11. Then, in Step S14, the dispensing amount of the buffer solution is determined by the conditional judgment as shown in FIG. 12. Thus, in this case, there exist the threshold values N1 and N2 for determining whether Fbg measurement is performed or not and the threshold values N3 and N4 for determining the dilution degree in Fbg measurement.

These threshold values can have a relation of N3<N1<N2<N4 (e.g., N1=150 (mg/dL), N2=600 (mg/dL), N3=50 (mg/dL), N4=700 (mg/dL)). In this case, the first range (N1 to N2) for determining whether Fbg measurement is performed or not is narrower than the second range (N3 to N4) for determining whether the dilution degree is higher or lower than the standard degree. However, N1 and N3 also may be an identical value and N2 and N4 also may be an identical value.

FIG. 13(c) illustrates a display example of the analysis result by the analysis operation procedure of the third example. The specimen number 10001 has the dFbg value in the range of N1<dFbg<N2 and thus no Fbg measurement is performed. On the other hand, the specimen number 10002 has the dFbg value that is larger than N2 and that deviates from the first range. Thus, Fbg measurement is performed but the dFbg value of the specimen number 10002 is within the second range. Thus, the Fbg measurement is performed at a standard dilution degree. The specimen numbers 10003 and 10004 have dFbg values deviating from both of the first range and the second range. Thus, the Fbg measurement is performed at a dilution degree higher or lower than the standard dilution degree. Thus, in the table, the column for [dFbg] displays symbols of "<" and ">" and the column for [Fbgsec] displays a symbol of "!".

Function and Effect of the Present Embodiment

In the above-described respective embodiments, a dFbg value is calculated using the detection result acquired by PT measurement. Thus, this dFbg value can be used as a substitute of Fbg. Accordingly, when the dFbg value is used as a substitute of Fbg, there is no need to perform an Fbg measurement using an exclusive reagent for measuring a fibrinogen concentration. This can consequently reduce the time and cost required for the measurement.

In the case of the first example and the third example for the analysis operation procedure in particular, the Fbg measurement is performed based on the dFbg value as required. This can consequently improve, in an efficient manner, both of the effect for reducing the time and cost required for the Fbg measurement and the reliability of the analysis result of the fibrinogen concentration.

Furthermore, in the case of the second example and the third example of the analysis operation procedure, the measurement condition (the dilution degree of the measurement sample) of the Fbg measurement is determined depending on the dFbg value. This can provide an Fbg measurement that effectively uses the dFbg value, and consequently can consequently eliminate the need to repeat an Fbg measurement while changing the dilution degree. Thus, the time and cost required for an Fbg measurement can be further reduced.

In the above-described embodiment, the dFbg value is calculated based on the ratio information A that reflects the ratio between the transmitted light intensity at the start of the clotting reaction and the transmitted light intensity at the end of the clotting reaction detected in PT measurement. Thus, even when the specimen includes a large amount of interfering substance such as chyle or bilirubin, a highly-accurate dFbg value can be calculated. This will be described in detail below.

When the dFbg is calculated based on a change amount of the scattered light from the measurement sample as disclosed in the prior art (Japanese Unexamined Patent Publication No. 58555/1985), the scattered light tends to be influenced by interfering substance (the interfering substance itself may be a scatterer), thus making it difficult to calculate an accurate dFbg.

When the dFbg is acquired by detecting the transmitted light transmitted through the measurement sample, the dFbg must be calculated in an actual case based on a change amount of the absorbance having a correlation with a fibrinogen concentration. However, this case is also remarkably influenced by interfering substance as described below.

Figure 15:
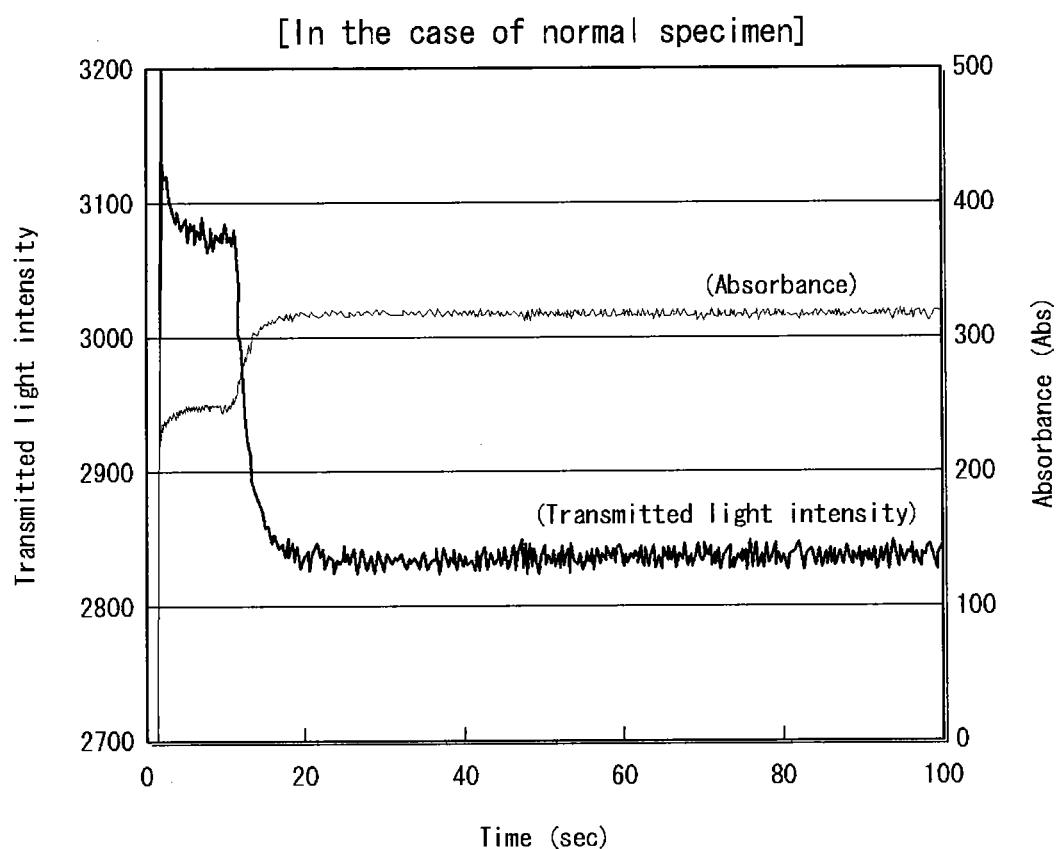
FIG. 15 is a clotting reaction curve illustrating the relation between an actually-measured value of the transmitted light intensity and time in the PT measurement by the blood coagulation analyzer.

FIG. 15 illustrates a clotting reaction curve showing the relation between the actually-measured value of the transmitted light intensity and time in PT measurement. In FIG. 15, the thick line shows a clotting reaction curve of the transmitted light intensity and a thin line shows a clotting reaction curve of the absorbance.

Generally, the absorbance Abs can be calculated by the following formula (3) based on the relation between the incident light intensity $L_0$ from the light source and the transmitted light intensity L.

$$Abs = \log_{10}(L_0/L) \quad (3)$$

Then, the change amount of the absorbance from the start of the clotting reaction to the end of the clotting reaction has a correlation with the fibrinogen concentration. Then, based on the change amount, the dFbg can be calculated using a standard curve for example.

Figure 16:
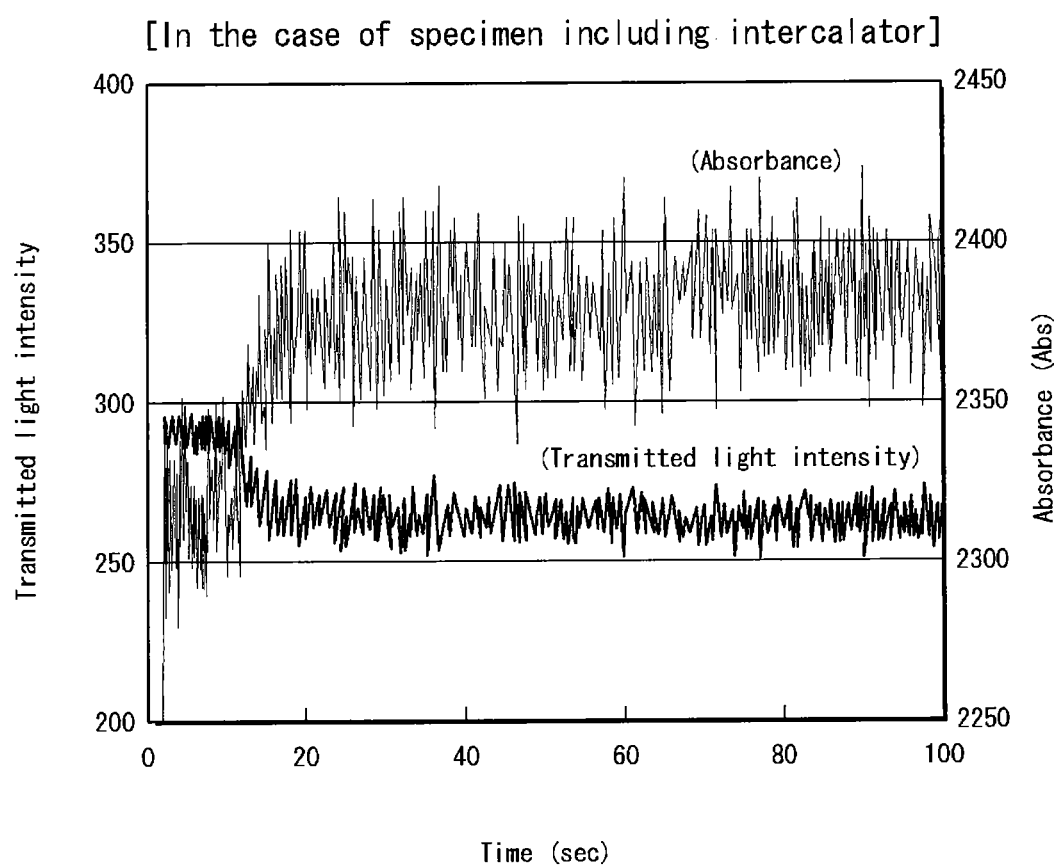
FIG. 16 is a clotting reaction curve illustrating the relation between the actually-measured value of the transmitted light intensity and time in a PT measurement using a specimen including interfering substance by the blood coagulation analyzer.

On the other hand, FIG. 16 illustrates a clotting reaction curve showing the relation, when a specimen including interfering substance is used to perform a PT measurement, between the actually-measured value of the transmitted light intensity and time. FIG. 16 also shows the clotting reaction curve of the absorbance by a thin line. When a specimen includes a large amount of interfering substance, values of both of a transmitted light intensity and an absorbance remarkably fluctuate, compared with a normal specimen including no interfering substance (see FIG. 15). Further, when a specimen includes a large amount of interfering substance, value and change amount of a transmitted light intensity are remarkably decreased, compared with a normal specimen including no interfering substance (see FIG. 15). The up-and-down fluctuation of the absorbance is extremely larger than the up-and-down fluctuation of the transmitted light intensity. Thus, on calculating the change amount of the absorbance from the start of the clotting reaction to the end of the clotting reaction, it is difficult to identify the clotting reaction starting level and the clotting reaction completion level, thus there is a high possibility of causing a large margin of error. This consequently decreases the reliability of the dFbg value calculated based on the change amount of the absorbance.

On the other hand, the transmitted light intensity has a smaller up-and-down fluctuation than that of the absorbance, even when the specimen includes interfering substance. Thus, the clotting reaction starting level and the clotting reaction completion level can be more easily identified, thus reducing errors. Thus, a highly-reliable dFbg value can be acquired based on ratio information A reflecting the ratio between the transmitted light intensity at the start of the clotting reaction and the transmitted light intensity at the end of the clotting reaction.

In the above-described embodiment, PT is calculated based on the clotting reaction curve for the transmitted light intensity. This clotting reaction curve has, as shown in FIG. 16, a smaller up-and-down fluctuation than that of the absorbance, even when the specimen includes a large amount of interfering substance. Therefore, the clotting reaction starting level and the clotting reaction end level can be calculated in a relatively accurate manner. Thus, the PT measurement can achieve improved reliability.

Furthermore, in the above-described embodiment, a derived fibrinogen concentration reflecting a fibrinogen concentration in the blood sample is acquired by a clotting reagent such as a prothrombin time measurement reagent (PT measurement reagent), a partial thromboplastin time measurement reagent (PTT measurement reagent), or an activated partial thromboplastin time measurement reagent (APTT measurement reagent). Then, whether the derived fibrinogen concentration is within a predetermined range or not is determined. Then, based on the determination result, the reagent for measuring a fibrinogen concentration is used to acquire a fibrinogen concentration in the blood sample. Accordingly, when the derived fibrinogen concentration is abnormal, a more accurate fibrinogen concentration can be acquired. When the derived fibrinogen concentration is normal on the other hand, the derived fibrinogen concentration can substitute for a fibrinogen concentration. Thus, no further preparation or measurement of a measurement sample for example is required, so that time and cost can be reduced.

Furthermore, depending on the derived fibrinogen concentration, the preparation condition for the measurement sample for measuring a fibrinogen concentration is set. Thus, the measurement sample can be prepared based on a condition reflecting the property of the blood sample that can be predicted based on the derived fibrinogen concentration. Accordingly, there is no need to change preparation conditions many times to prepare a measurement sample; this can consequently reduce the time and cost required for the fibrinogen concentration measurement using the reagent for measuring a fibrinogen concentration.

Furthermore, in the above-described embodiment, a derived fibrinogen concentration reflecting a fibrinogen concentration in the blood sample is acquired by a clotting reagent such as a prothrombin time measurement reagent (PT measurement reagent), a partial thromboplastin time measurement reagent (PTT measurement reagent), or an activated partial thromboplastin time measurement reagent (APTT measurement reagent). Then, a reagent for measuring a fibrinogen concentration is used to acquire a fibrinogen concentration in the blood sample. Then, the measurement sample for acquiring the fibrinogen concentration is prepared based on a condition depending on the derived fibrinogen concentration. Thus, a measurement sample for measuring a fibrinogen concentration can be prepared based on a condition reflecting the property of a blood sample that can be predicted from the derived fibrinogen concentration. Accordingly, there is no need to change preparation conditions many times to prepare a measurement sample; this can consequently reduce the time and cost required for the measurement of a fibrinogen concentration using the reagent for measuring a fibrinogen concentration.

Furthermore, in the above-described embodiment, depending on the derived fibrinogen concentration, the concentration of the blood sample in a measurement sample for measuring a fibrinogen concentration is changed. Specifically, when the derived fibrinogen concentration is larger than the first threshold value, the concentration of the blood sample in a measurement sample for measuring a fibrinogen concentration is reduced to a value smaller than a predetermined value. When the derived fibrinogen concentration is smaller than the second threshold value smaller than the first threshold value, the concentration of the blood sample in a measurement sample for measuring a fibrinogen concentration is changed to a value larger than the predetermined value. According to this configuration, a derived fibrinogen concentration larger than the first threshold value can provide a prediction that the blood sample has a high fibrinogen concentration. Thus, the concentration of the blood sample in a measurement sample for measuring a fibrinogen concentration is reduced in advance. A derived fibrinogen concentration smaller than the second threshold value can provide a prediction that the blood sample has a low fibrinogen concentration. Thus, the concentration of the blood sample in a measurement sample for measuring a fibrinogen concentration is increased in advance. This can consequently provide a measurement by a measurement sample for measuring a fibrinogen concentration with a dilution degree appropriate for the property of the blood sample. This can eliminate the need to change dilution degrees many times to prepare the two measurement samples.

Furthermore, the above-described embodiment includes a display section; and a display control means for causing the display section to display at least one of a derived fibrinogen concentration and a fibrinogen concentration in a manner to discriminate between a derived fibrinogen concentration as a value obtained from a measurement sample for measuring a derived fibrinogen concentration and a fibrinogen concentration as a value obtained from a measurement sample for measuring a fibrinogen concentration. Thus, a user can, by looking at the display of the display section, clearly discriminate the derived fibrinogen concentration from the fibrinogen concentration.

Furthermore, the above-described embodiment includes a display section; and a display control means for causing the display section to display, when a derived fibrinogen concentration is larger than a first threshold value, information showing that the derived fibrinogen concentration is larger than the first threshold value and, when a derived fibrinogen concentration is smaller than a second threshold value, information showing that the derived fibrinogen concentration is smaller than the second threshold value. Thus, the user can, by looking at the display of the display section, clearly discriminate whether the derived fibrinogen concentration is larger than the first threshold value or is smaller than the second threshold value.

Furthermore, in the above-described embodiment, a sample preparation section includes a dispensing section for dispensing a blood sample to a cuvette (storage container) from a test tube (sample container) for containing a blood sample. The control section controls the sample preparation section so that a part of the blood sample contained in the storage container is dispensed to the first reaction container and a measurement sample for measuring a derived fibrinogen concentration is prepared in the first reaction container. The control section controls the sample preparation section so that another part of the blood sample contained in the storage container is dispensed to the second reaction container and a measurement sample for measuring a fibrinogen concentration is prepared in the second reaction container. By this configuration, the same blood sample can be dispensed multiple times as required from a storage container to perform a measurement. Thus, even when the sample container is at a position away from a position at which the suction by the dispensing section is performed, a measurement can be performed again as required and thus the processing by the blood coagulation analyzer can be performed at a higher speed.

Furthermore, in the above-described embodiment, light transmitted through a measurement sample prepared using a clotting reagent such as a PT measurement reagent or an APTT measurement reagent is detected by the detecting section. Then, ratio information is acquired based on the ratio between the first value (the transmitted light intensity at the start of the clotting reaction) and the second value (the transmitted light intensity at the end of the clotting reaction) reflecting the intensity of the transmitted light. Based on this ratio information, a fibrinogen concentration in the blood sample (in other words, a dFbg value) is acquired. Since scattered light is easily influenced by interfering substance, the detection of transmitted light from the measurement sample is more useful to reduce the influence by the interfering substance, thus permitting to accurately acquire the fibrinogen concentration. Furthermore, the ratio information regarding the first value and the second value reflecting the intensity of the transmitted light has a correlation with a fibrinogen concentration. Furthermore, the ratio information is insusceptible to interfering substance. Thus, by acquiring the fibrinogen concentration based on the ratio information reflecting the ratio between the first value and the second value, the fibrinogen concentration can be accurately calculated even in the case of a blood sample including a large amount of interfering substance. Furthermore, since there is no need to measure a fibrinogen concentration using an exclusive reagent for measuring a fibrinogen concentration, the time and cost required for the measurement can be reduced.

Since the first value is a value reflecting the intensity of the light transmitted through the measurement sample at the start of a clotting reaction, and the second value is a value reflecting the intensity of the light transmitted through the measurement sample at the end of a clotting reaction, the fibrinogen concentration can be acquired more accurately.

Furthermore, in the above-described embodiment, the first value and the second value are values showing the light intensity of transmitted light detected by the detecting section. The transmitted light amount, which reflects the intensity of the transmitted light, is insusceptible to the interfering substance in a blood sample compared with absorbance similarly reflecting the intensity of the transmitted light. Thus, by using the transmitted light intensity as the first value and the second value, the fibrinogen concentration can be acquired more accurately.

Furthermore, in the above-described embodiment, there is provided a hard disk (memory section) that memorizes a standard curve showing the correlation between the ratio information and a fibrinogen concentration in the blood sample. The control section acquires a fibrinogen concentration in the blood sample based on the standard curve and the ratio information. Furthermore, the control section multiplies the ratio information by a predetermined coefficient to thereby acquire the fibrinogen concentration in the blood sample. Thus, either method can be used to accurately acquire a fibrinogen concentration.

Furthermore, in the above-described embodiment, PT, PTT, or APTT is acquired based on the transmitted light detected by the detecting section. Thus, the fibrinogen concentration can be acquired based on the transmitted light obtained from PT measurement, PTT measurement or APTT measurement.

Furthermore, in the above-described embodiment, the end of the clotting reaction of the blood sample is detected based on the light intensity of transmitted light detected by the detecting section. Thus, by detecting the end of the clotting reaction based on the light intensity of transmitted light insusceptible to interfering substance, the clotting time of PT or APTT for example and the fibrinogen concentration can be acquired more accurately with regard to a blood sample including interfering substance.

Other Modified Examples of the Present Invention

The present invention can be variously designed appropriately without being limited to the above-described embodiment.

In the above-described embodiment, "clotting reagent" means a reagent used to promote the clotting of a blood sample. For example, PT measurement reagent such as Thrombocheck® PT (produced by SYSMEX CORPORATION) and APTT measurement reagent such as Thrombocheck APTT (produced by SYSMEX CORPORATION) can be used.

Although in the above-described embodiment a dFbg value is acquired by using a measurement result obtained in PT measurement, a dFbg value also may be acquired by using the measurement result obtained through PTT measurement or APTT measurement.

Furthermore, although in the above-described embodiment a dFbg value is acquired by using a standard curve showing the correlation between the ratio information A and the fibrinogen concentration, a dFbg value also may be acquired by multiplying the ratio information A by the coefficient showing the inclination of the standard curve.

Although in the above-described embodiment a dFbg value is acquired based on the ratio between the transmitted light intensity detected at the start of the clotting reaction and the transmitted light intensity detected at the end of the clotting reaction, a dFbg value also may be acquired based on the ratio between the absorbance at the start of the clotting reaction and the absorbance at the end of the clotting reaction. In this case, in order to reduce the influence by interfering substance, it is preferable to acquire the transmitted light intensities at the start of the clotting reaction and at the end of the clotting reaction based on the clotting reaction curve for the transmitted light intensity obtained through PT measurement as described above; to calculate the absorbance at the start of the clotting reaction based on the transmitted light intensity at the start of the clotting reaction; to calculate the absorbance at the end of the clotting reaction based on the transmitted light intensity at the end of the clotting reaction; and to acquire, based on the respective calculated absorbances, the ratio between the absorbance at the start of the clotting reaction and the absorbance at the end of the clotting reaction.

Furthermore, although in the above-described embodiment a dFbg value is acquired based on the ratio between the transmitted light intensity detected at a time point at which a clotting reaction starts and the transmitted light intensity detected at a time point at which a clotting reaction ends, the transmitted light intensity at any time point (e.g., an arbitrary time point prior to the start of a clotting reaction or a time point immediately after the start of a clotting reaction) can be used instead of the transmitted light intensity detected at a time point at which a clotting reaction starts so long as the time point can provide the detection of a similar transmitted light intensity to the transmitted light intensity detected at a time point at which a clotting reaction starts. Furthermore, instead of the transmitted light intensity detected at a time point at which a clotting reaction ends, the transmitted light intensity at any time point (e.g., a time point immediately before the end of a clotting reaction or an arbitrary time point after the end of a clotting reaction) can be used so long as the time point can provide the detection of a similar transmitted light intensity to the transmitted light intensity detected at a point at which a clotting reaction ends.

Furthermore, the blood coagulation analyzer 1 of the present invention acquires a dFbg value based on the ratio between the transmitted light intensity detected at the start of the clotting reaction and the transmitted light intensity detected at the end of the clotting reaction. Depending on the acquired dFbg value, whether an Fbg measurement is required or not is determined, or a condition for preparing a measurement sample for an Fbg measurement is changed. However, whether an Fbg measurement is required or not also may be determined, or a condition for preparing a measurement sample for an Fbg measurement also may be changed depending on a dFbg value obtained from the amount of change in the scattered light from the start of the clotting reaction to the end of the clotting reaction, or on a dFbg value obtained from the amount of change of the absorbance from the start of the clotting reaction to the end of the clotting reaction.

Furthermore, in the above-described embodiment, the control section 4a of the control apparatus 4 executes a processing for acquiring a dFbg value, a processing for determining whether a dFbg value is within a predetermined range or not, and a processing for acquiring a fibrinogen concentration based on the data obtained through Fbg measurement, and the control section 120 of the measurement apparatus executes a processing for controlling the preparation of a measurement sample and a processing for detecting the transmitted light from the measurement sample. However, these processings also may be entirely performed by a single control section.

Furthermore, in the above-described embodiment, the control section 4a of the control apparatus 4 executes a processing for acquiring the ratio information A reflecting the ratio between the transmitted light intensity at the start of the clotting reaction and the transmitted light intensity at the end of the clotting reaction and a processing for acquiring a dFbg value based on the ratio information A. However, the processing for acquiring the ratio information A and the processing for acquiring a dFbg value based on the ratio information A also may be performed by different control sections.

What is claimed is:

1. A blood coagulation analyzer comprising:
    a sample preparation section for preparing a measurement sample from a blood sample and a prothrombin time measurement reagent, a partial thromboplastin time measurement reagent, or an activated partial thromboplastin time measurement reagent;
    a control section that controls operations of each mechanism of the sample preparation section; and
    a detector including:
        a light source for emitting light to the prepared measurement sample; and
        a light-receiving section for receiving light transmitted through the measurement sample and converting the received light into an electric signal, wherein the detector outputs a data reflecting an intensity of the received light;
    a computer coupled to the sample preparation section and analyzing information of the measurement sample obtained by the sample preparation section, the computer comprising;
        a processor; and
        a computer readable medium storing a computer program, wherein the processor is programmed to execute the computer program to perform operations comprising:
            receiving the data reflecting an intensity of the received light from the detector;
            calculating a first intensity (L1) of a light transmitted through the measurement sample detected at a clotting reaction starting stage;
            calculating a second intensity (L2) of a light transmitted through the measurement sample detected at a clotting reaction ending stage;
            calculating a ratio between the first intensity (L1) and the second intensity (L2);
            calculating ratio information (A) reflecting a logarithm of the ratio; and
            acquiring, based on the ratio information (A) and a standard curve showing a correlation between the ratio information and a fibrinogen concentration in the blood sample, a value corresponding to a fibrinogen concentration in the blood sample.

2. The blood coagulation analyzer according to claim 1, wherein the clotting reaction starting stage comprises a time point at which a clotting reaction starts and all time zones within which transmitted light having the similar light intensity to the first intensity are detected.

3. The blood coagulation analyzer according to claim 1, wherein the clotting reaction ending stage comprises a time point at which a clotting reaction ends and all time zones within which transmitted light having the similar light intensity to the second intensity are detected.

4. The blood coagulation analyzer according to claim 3, wherein calculating the ratio information (A) is further represented by the following formula $$A=\log_{10}(L1/L2).$$

5. The blood coagulation analyzer according to claim 1, wherein the processor is further programmed to execute the computer program performing operations to acquire a prothrombin time, a partial thromboplastin time, or an activated partial thromboplastin time based on the data output from the detector.

6. The blood coagulation analyzer according to claim 1, wherein the processor is further programmed to execute the computer program to detect, based on the data output from the detector, the end of the clotting reaction of the blood sample.

7. The blood coagulation analyzer according to claim 1, further comprising:
    determining whether the acquired value is within a predetermined range; and
    sending an instruction to acquire a fibrinogen concentration using a fibrinogen concentration measurement reagent to the control section.

8. The blood coagulation analyzer according to claim 7, wherein sending the instruction to acquire the fibrinogen concentration comprises sending the instruction to acquire concentration upon determination that the acquired value is out of the predetermined range.

9. A blood coagulation analyzer comprising:
    a sample preparation section for preparing a measurement sample from a blood sample and a prothrombin time measurement reagent, a partial thromboplastin time measurement reagent, or an activated partial thromboplastin time measurement reagent; a control section that controls operations of each mechanism of the sample preparation section; and
    a detector including:
        a light source for emitting light to the prepared measurement sample; and
        a light-receiving section for receiving light transmitted through the measurement sample and converting the received light into an electric signal, wherein the detector outputs a data reflecting an intensity of the received light;
    a computer coupled to the sample preparation section and analyzing information of the measurement sample obtained by the sample preparation section, the computer comprising;
        a processor; and
        a computer readable medium storing a computer program, wherein the processor is programmed to execute the computer program to perform operations comprising:
            receiving the data reflecting an intensity of the received light from the detector;
            calculating a first intensity (L1) of a light transmitted through the measurement sample detected at a clotting reaction starting stage;
            calculating a second intensity (L2) of a light transmitted through the measurement sample detected at a clotting reaction ending stage;
            calculating a ratio between the first intensity (L1) and the second intensity (L2);
            calculating ratio information (A) reflecting a logarithm of the ratio; and
            acquiring a value corresponding to a fibrinogen concentration in the blood sample by multiplying the ratio information (A) by a predetermined coefficient.

10. The blood coagulation analyzer according to claim 9, further comprising:
    determining whether the acquired value is within a predetermined range; and
    sending an instruction to acquire a fibrinogen concentration using a fibrinogen concentration measurement reagent to the control section.

11. The blood coagulation analyzer according to claim 10, wherein sending the instruction to acquire the fibrinogen concentration comprises sending the instruction to acquire concentration upon determination that the acquired value is out of the predetermined range.

12. The blood coagulation analyzer according to claim 9, wherein calculating the ratio information (A) is further represented by the following formula $$A = \log_{10}(L1/L2).$$

* * * * *